(12) United States Patent
Way

(10) Patent No.: US 7,820,155 B2
(45) Date of Patent: Oct. 26, 2010

(54) METHODS OF TREATING CANCER COMPRISING ADMINISTERING AN INTERLEUKIN-6 ANTIBODY VARIABLE REGION

(75) Inventor: Jeffrey Way, Cambridge, MA (US)

(73) Assignee: Merck Patent GmbH, Darmstadt (DE)

( * ) Notice: Subject to any disclaimer, the term of this patent is extended or adjusted under 35 U.S.C. 154(b) by 432 days.

(21) Appl. No.: 11/647,992

(22) Filed: Dec. 29, 2006

(65) Prior Publication Data
US 2007/0178098 A1    Aug. 2, 2007

Related U.S. Application Data

(60) Provisional application No. 60/755,383, filed on Dec. 30, 2005.

(51) Int. Cl.
*A61K 16/24* (2006.01)
(52) U.S. Cl. .................. 424/85.2; 424/141.1; 424/145.1
(58) Field of Classification Search ....................... None
See application file for complete search history.

(56) References Cited

U.S. PATENT DOCUMENTS

| | | | |
|---|---|---|---|
| 6,086,874 | A | 7/2000 | Yoshida et al. |
| 6,969,517 | B2 | 11/2005 | Gillies et al. |
| 2006/0257407 | A1 | 11/2006 | Chen et al. |

FOREIGN PATENT DOCUMENTS

| | | |
|---|---|---|
| WO | WO-0107081 | 2/2001 |
| WO | WO-02072605 | 9/2002 |
| WO | WO-2004039826 | 5/2004 |
| WO | WO-2004045507 | 6/2004 |
| WO | WO-2004071404 | 8/2004 |
| WO | WO-2005005638 | 1/2005 |

OTHER PUBLICATIONS

Beers and Berkow (1999). The Merck Manual of Diagnosis and Therapy, 17$^{th}$ edition, pp. 986-995.*
Chuntharapai et al (1997) Method in Enzymology, vol. 288, pp. 15-27.*
BD Pharmingen, (2006) "Technical Data Sheet: Purified Rat Anti-Human IL-6 Monoclonal Antibody (ELISA Capture)," Catalog No. 554543, 0.5 mg.
Boulanger, M.J. et al., (2003) "Hexameric structure and assembly of the interleukin-6/IL-6 α-Receptor/gp130 complex " *Science* 300:2101-2104.
Brakenhoff, J. et al., (1990) "Structure-Function analysis of human IL-6: epitope mapping of neutralizing monoclonal antibodies with amino- and carboxyl-terminal deletion mutants," *J. Immunol.* 145(2):561-568.
Davies, J. et al., (1996) "Affinity improvement of single antibody VH domains: residues in all three hypervariable regions affect antigen binding," *Immunotechnology* 2(3):169-179.
eBioscience, (2007) "Product Information: Functional Grade Purified anti-human interleukin-6 (IL6)," Catalog No. 16-7069.
Fischer, M. et al., (1997) "A bioactive designer cytokine for human hematopoietic progenitor cell expansion," *Nat. Biotechnol.* 15:142-145.
Georgii-Hemming, P. et al., (1996) "Insulin-like growth factor I is a growth and survival factor in human multiple myeloma cell lines," *Blood* 88:2250-2258.
Gillies, S. et al., (1989) "High-level expression of chimeric antibodies using adapted cDNA variable region cassettes," *J. Immunol. Methods* 125(1-2):191-202.
Holt, L. J. et al., (2003) "Domain antibodies: proteins for therapy," *Trends Biotechnol.* 21(11):484-490.
International Preliminary Report on Patentability for international application No. PCT/EP2006/012236, issued by the International Bureau of WIPO on Jul. 1, 2008, 14 pages.
International Search Report for application No. PCT/EP2006/012236, mailed from the European Patent Office as International Searching Authority on May 21, 2007, 6 pages.
Köhler, G. et al., (1975) "Continuous cultures of fused cells secreting antibody of predefined specificity," *Nature* 256:495-497.
Lehrnbecher et al., (1999) "Assessment of Measuring Circulating Levels of Interleukin-6, Interleukin-8, C-Reactive Protein, Soluble Fcγ Receptor Type III, and Mannose-Binding Protein in Febrile Children with Cancer and Neutropenia," *Clin. Infect. Dis.* 29:414-9.
Little, M. et al., (2000) Of mice and men: hybridoma and recombinant antibodies: *Immunol. Today* 21(8):364-370.
Peters, M. et al., (1998) "In vivo and in vitro activities of the gp130-stimulating designer cytokine hyper-IL-6," *J. Immunol.* 161:3575-3581.
Scheller, J. et al., (2004) "Development of a monoclonal antibody-based enzyme-linked immunoabsorbent assay for the binding of gp130 to the IL-6/IL-6R complex and its competitive inhibition," *J. Immunol. Methods* 291:93-100.
van de Winkel, J. G. J. et al., (1993) "Human IgG Fc receptor heterogeneity: molecular aspects and clinical implications," *Immunol. Today* 14(5):215-221.
van Zaanen, H.C.T. et al., (1996) "Endogenous interleukin 6 production in multiple myeloma patients treated with chimeric monoclonal anti-IL6 antibodies indicates the existence of a positive feed-back loop," *J. Clin. Invest.* 98(6):1441-1448.
Wyant, T. et al., (1999) "Potent immunoregulatory effects of *Salmonella typhi* flagella on antigenic stimulation of human peripheral blood mononuclear cells," *Infect. Immun.* 67(3): 1338-1346.
Zaki, M. et al., (2004) "CNTO 328, a monoclonal antibody to IL-6, inhibits human tumor-induced cachexia in nude mice," *Int. J. Cancer* 111:592-595.
Zou, J.P. et al., (1999) "Human Glioma-Induced Immunosuppression Involves Soluble Factor(s) That Alters Monocyte Cytokine Profile and Surface Markers," *J. Immunol.* 162: 4882-4892.

* cited by examiner

*Primary Examiner*—Prema Mertz
(74) *Attorney, Agent, or Firm*—Goodwin Procter LLP

(57) ABSTRACT

The present invention provides an isolated IL-6 antagonist including an antibody variable region that prevents IL-6 from binding to gp130. The present invention also provides compositions and methods for treating IL-6 related diseases based on the IL-6 antagonists of the invention.

2 Claims, 15 Drawing Sheets

Figure 1. The method of treatment of the invention.
A. No treatment
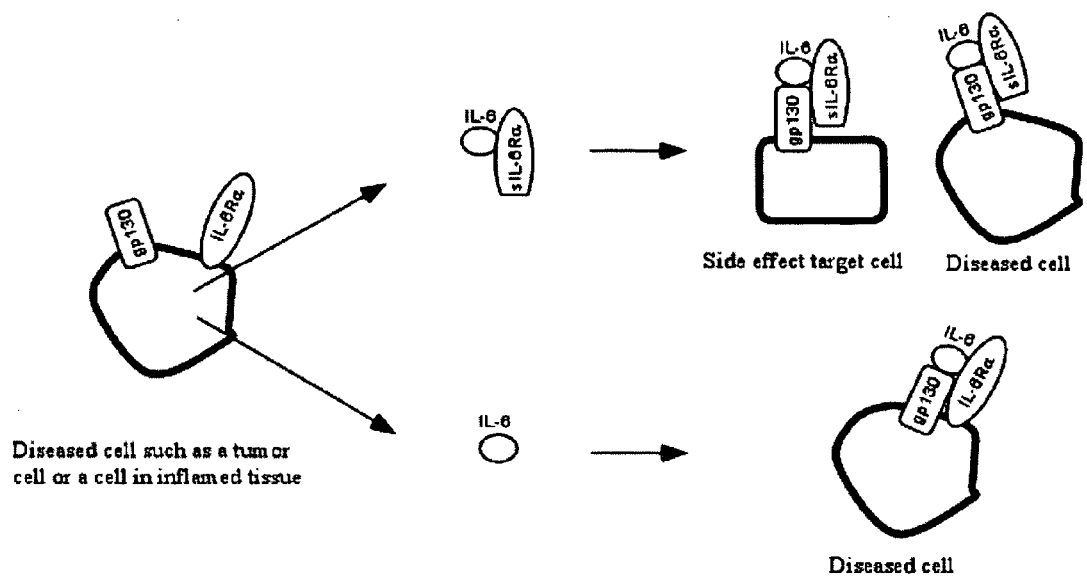
B. Treatment with an antibody of the invention
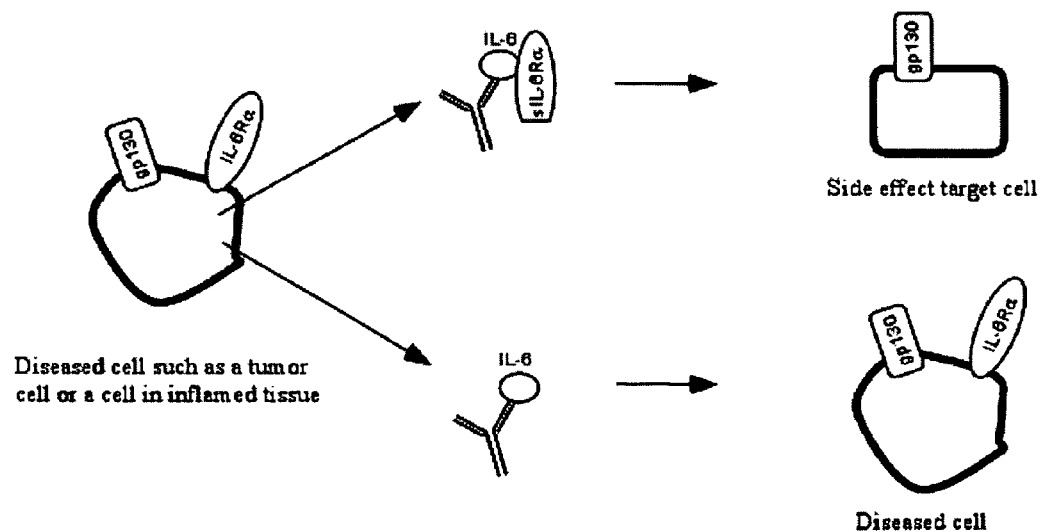

Figure 2. Alignment of antibody V region sequences that bind to IL-6 and block interaction with gp130. Positions variation among the sequences are indicated with arrows. The CDRs are boxed.

Light chains

```
Mab#195 Vk   (1)  DIVLTQSPASLAVSLGQRATISCRASESVDNFGISFMNWFQQKPGQPPKL   (SEQ ID NO:29)
Mab#309 Vk   (1)  DIVLTQSPASLAVSLGQRATISCRASESVGNFGISFMNWFQQKPGQPPKL   (SEQ ID NO:30)
Mab#471 Vk   (1)  DIVLTQSPASLAVSLGQRATISCRASESVGNFGISFMNWFQQKPGQPPKL   (SEQ ID NO:31)
Mab#476 Vk   (1)  DIVLTQSPASLAVSLGQRATISCRASESVHNFGISFMNWFQQKPGQPPKL   (SEQ ID NO:32)

Mab#195 Vk   (51) LIYVASNQGSGVPARFSGSGSGTDFSLNIHPMEEDDTAMYFCQQSKEVPW   (SEQ ID NO:29)
Mab#309 Vk   (51) LIYTASNQGSGVPARFSGSGSGTDFSLNIHPMEEDDSAMYFCQQSKEVPW   (SEQ ID NO:30)
Mab#471 Vk   (51) LIYTASNQGSGVPARFSGSGSGTDFSLNIHPMEEDDSAMYFCQQSKEIPW   (SEQ ID NO:31)
Mab#476 Vk   (51) LIYTASNQGSGVPARFSGSGSGTDFSLNIHPVEEDDTAMYFCQQGKEVPW   (SEQ ID NO:32)

Mab#195 Vk  (101) TFGGGTKLEIK   (SEQ ID NO:29)
Mab#309 Vk  (101) TFGGGTKLEIK   (SEQ ID NO:30)
Mab#471 Vk  (101) TFGGGTKLEIK   (SEQ ID NO:31)
Mab#476 Vk  (101) TFGGGTKLEIK   (SEQ ID NO:32)
```

Heavy chains

```
Mab#195 VH   (1)  EVKLEESGGGLVQPGGSMKLSCVASGFTFSNYWMNWVRQSPEKGLEWVAE   (SEQ ID NO:33)
Mab#309 VH   (1)  EVKLEESGGGLVQPGGSMKLSCVASGFTFSNYWMNWVRQSPEKGLEWVAE   (SEQ ID NO:34)
Mab#471 VH   (1)  EVKFEESGGGLVQPGGSMKLSCVASGFSFSNYWMNWVRQSPEKGLEWVAE   (SEQ ID NO:35)
Mab#476 VH   (1)  EVKLEESGGGLVQPGGSMKLSCAASGFTFSDAWMDWVRQSPEKGLEWVAE   (SEQ ID NO:36)

Mab#195 VH   (51) IRLKSNNYATHYAESVKGRFTISRDDSKSSVYLQMNNLRAEDTGIYYCTR   (SEQ ID NO:33)
Mab#309 VH   (51) IRLKSNKGATHYAESVKGRFTISRDDSKSSVYLQMNNLRAEDTGIYYCAS   (SEQ ID NO:34)
Mab#471 VH   (51) IRLTSNKQAIYYAESVKGRFTISRDDSKSSVYLQMNNLRAEDTGIYYCAS   (SEQ ID NO:35)
Mab#476 VH   (51) IRSKANNHATYYAESVKGRFTISRDDSKSSVYLQMNSLRAEDTGIYYCTT   (SEQ ID NO:36)

Mab#195 VH  (101) EDYYGYPDYWGQGTTLTVSS   (SEQ ID NO:33)
Mab#309 VH  (101) LLYDGY-LHWGQGTLVTVSA   (SEQ ID NO:34)
Mab#471 VH  (101) LFYDGY-LHWGQGTLVTVSA   (SEQ ID NO:35)
Mab#476 VH  (101) PTLYGAMDYWGQGTSVTVSA   (SEQ ID NO:36)
```

Figure 3. Schematic depiction of the proteins used herein.
A. Fc-IL6Ralpha-IL6   B. Fc-IL6   C. Fc-IL6Ralpha
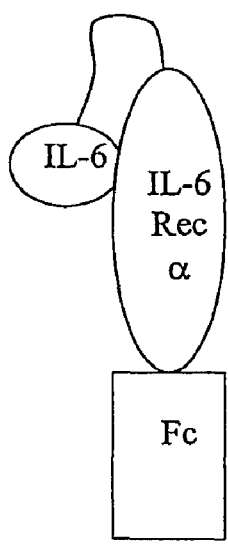
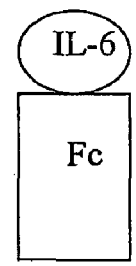
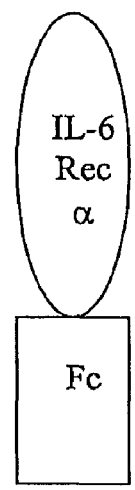

Figure 12. In vivo inhibition haptoglobin secretion.

SEQUENCE LISTING

```
<160> NUMBER OF SEQ ID NOS: 62

<210> SEQ ID NO 1
<211> LENGTH: 9
<212> TYPE: PRT
<213> ORGANISM: Artificial Sequence
<220> FEATURE:
<223> OTHER INFORMATION: synthetic: designed sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
```

```
<400> SEQUENCE: 1

Phe Xaa Phe Ser Xaa Xaa Trp Met Xaa
1               5

<210> SEQ ID NO 2
<211> LENGTH: 9
<212> TYPE: PRT
<213> ORGANISM: Artificial Sequence
<220> FEATURE:
<223> OTHER INFORMATION: synthetic: designed sequence

<400> SEQUENCE: 2

Phe Thr Phe Ser Asn Tyr Trp Met Asn
1               5

<210> SEQ ID NO 3
<211> LENGTH: 9
<212> TYPE: PRT
<213> ORGANISM: Artificial Sequence
<220> FEATURE:
<223> OTHER INFORMATION: synthetic: designed sequence

<400> SEQUENCE: 3

Phe Ser Phe Ser Asn Tyr Trp Met Asn
1               5

<210> SEQ ID NO 4
<211> LENGTH: 9
<212> TYPE: PRT
<213> ORGANISM: Artificial Sequence
<220> FEATURE:
<223> OTHER INFORMATION: synthetic: designed sequence

<400> SEQUENCE: 4

Phe Thr Phe Ser Asp Ala Trp Met Asp
1               5

<210> SEQ ID NO 5
<211> LENGTH: 19
<212> TYPE: PRT
<213> ORGANISM: Artificial Sequence
<220> FEATURE:
<223> OTHER INFORMATION: synthetic: designed sequence
<220> FEATURE:
<221> NAME/KEY: misc_feature
<222> LOCATION: (4)..(6)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid

<400> SEQUENCE: 5

Glu Ile Arg Xaa Xaa Xaa Asn Xaa Xaa Ala Xaa Xaa Tyr Ala Glu Ser
1               5                   10                  15

Val Lys Gly

<210> SEQ ID NO 6
<211> LENGTH: 19
<212> TYPE: PRT
<213> ORGANISM: Artificial Sequence
<220> FEATURE:
<223> OTHER INFORMATION: synthetic: designed sequence
```

```
<400> SEQUENCE: 6

Glu Ile Arg Leu Lys Ser Asn Asn Tyr Ala Thr His Tyr Ala Glu Ser
1               5                   10                  15

Val Lys Gly

<210> SEQ ID NO 7
<211> LENGTH: 19
<212> TYPE: PRT
<213> ORGANISM: Artificial Sequence
<220> FEATURE:
<223> OTHER INFORMATION: synthetic: designed sequence

<400> SEQUENCE: 7

Glu Ile Arg Leu Lys Ser Asn Lys Gly Ala Thr His Tyr Ala Glu Ser
1               5                   10                  15

Val Lys Gly

<210> SEQ ID NO 8
<211> LENGTH: 19
<212> TYPE: PRT
<213> ORGANISM: Artificial Sequence
<220> FEATURE:
<223> OTHER INFORMATION: synthetic: designed sequence

<400> SEQUENCE: 8

Glu Ile Arg Leu Thr Ser Asn Lys Gln Ala Ile Tyr Tyr Ala Glu Ser
1               5                   10                  15

Val Lys Gly

<210> SEQ ID NO 9
<211> LENGTH: 19
<212> TYPE: PRT
<213> ORGANISM: Artificial Sequence
<220> FEATURE:
<223> OTHER INFORMATION: synthetic: designed sequence

<400> SEQUENCE: 9

Glu Ile Arg Ser Lys Ala Asn Asn His Ala Thr Tyr Tyr Ala Glu Ser
1               5                   10                  15

Val Lys Gly

<210> SEQ ID NO 10
<211> LENGTH: 9
<212> TYPE: PRT
<213> ORGANISM: Artificial Sequence
<220> FEATURE:
<223> OTHER INFORMATION: synthetic: designed sequence
<220> FEATURE:
<221> NAME/KEY: misc_feature
<222> LOCATION: (1)..(4)
<223> OTHER INFORMATION: Xaa can be any naturally occurring amino acid
<220> FEATURE:
<221> NAME/KEY: misc_feature
<222> LOCATION: (6)..(9)
<223> OTHER INFORMATION: Xaa can be any naturally occurring amino acid

<400> SEQUENCE: 10

Xaa Xaa Xaa Xaa Gly Xaa Xaa Xaa Xaa
1               5

<210> SEQ ID NO 11
<211> LENGTH: 9
<212> TYPE: PRT
<213> ORGANISM: Artificial Sequence
<220> FEATURE:
```

```
<223> OTHER INFORMATION: synthetic: designed sequence

<400> SEQUENCE: 11

Glu Asp Tyr Tyr Gly Tyr Pro Asp Tyr
1               5

<210> SEQ ID NO 12
<211> LENGTH: 8
<212> TYPE: PRT
<213> ORGANISM: Artificial Sequence
<220> FEATURE:
<223> OTHER INFORMATION: synthetic: designed sequence

<400> SEQUENCE: 12

Leu Leu Tyr Asp Gly Tyr Leu His
1               5

<210> SEQ ID NO 13
<211> LENGTH: 8
<212> TYPE: PRT
<213> ORGANISM: Artificial Sequence
<220> FEATURE:
<223> OTHER INFORMATION: synthetic: designed sequence

<400> SEQUENCE: 13

Leu Phe Tyr Asp Gly Tyr Leu His
1               5

<210> SEQ ID NO 14
<211> LENGTH: 9
<212> TYPE: PRT
<213> ORGANISM: Artificial Sequence
<220> FEATURE:
<223> OTHER INFORMATION: synthetic: designed sequence

<400> SEQUENCE: 14

Pro Thr Leu Tyr Gly Ala Met Asp Tyr
1               5

<210> SEQ ID NO 15
<211> LENGTH: 14
<212> TYPE: PRT
<213> ORGANISM: Artificial Sequence
<220> FEATURE:
<223> OTHER INFORMATION: synthetic: designed sequence
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 15

Arg Ala Ser Glu Ser Val Xaa Asn Xaa Gly Ile Ser Phe Met
1               5                   10

<210> SEQ ID NO 16
<211> LENGTH: 14
<212> TYPE: PRT
<213> ORGANISM: Artificial Sequence
<220> FEATURE:
<223> OTHER INFORMATION: synthetic: designed sequence

<400> SEQUENCE: 16

Arg Ala Ser Glu Ser Val Asp Asn Phe Gly Ile Ser Phe Met
1               5                   10
```

<210> SEQ ID NO 17
<211> LENGTH: 14
<212> TYPE: PRT
<213> ORGANISM: Artificial Sequence
<220> FEATURE:
<223> OTHER INFORMATION: synthetic: designed sequence

<400> SEQUENCE: 17

Arg Ala Ser Glu Ser Val Gly Asn Phe Gly Ile Ser Phe Met
1               5                   10

<210> SEQ ID NO 18
<211> LENGTH: 14
<212> TYPE: PRT
<213> ORGANISM: Artificial Sequence
<220> FEATURE:
<223> OTHER INFORMATION: synthetic: designed sequence

<400> SEQUENCE: 18

Arg Ala Ser Glu Ser Val His Asn Phe Gly Ile Ser Phe Met
1               5                   10

<210> SEQ ID NO 19
<211> LENGTH: 14
<212> TYPE: PRT
<213> ORGANISM: Artificial Sequence
<220> FEATURE:
<223> OTHER INFORMATION: synthetic: designed sequence

<400> SEQUENCE: 19

Arg Ala Ser Glu Ser Val Asp Asn Tyr Gly Ile Ser Phe Met
1               5                   10

<210> SEQ ID NO 20
<211> LENGTH: 7
<212> TYPE: PRT
<213> ORGANISM: Artificial Sequence
<220> FEATURE:
<223> OTHER INFORMATION: synthetic: designed sequence
<220> FEATURE:
<221> NAME/KEY: misc_feature
<222> LOCATION: (1)..(1)
<223> OTHER INFORMATION: Xaa can be any naturally occurring amino acid

<400> SEQUENCE: 20

Xaa Ala Ser Asn Gln Gly Ser
1               5

<210> SEQ ID NO 21
<211> LENGTH: 7
<212> TYPE: PRT
<213> ORGANISM: Artificial Sequence
<220> FEATURE:
<223> OTHER INFORMATION: synthetic: designed sequence

<400> SEQUENCE: 21

Thr Ala Ser Asn Gln Gly Ser
1               5

<210> SEQ ID NO 22
<211> LENGTH: 7
<212> TYPE: PRT
<213> ORGANISM: Artificial Sequence
<220> FEATURE:
<223> OTHER INFORMATION: synthetic: designed sequence

<400> SEQUENCE: 22

```
Val Ala Ser Asn Gln Gly Ser
1               5

<210> SEQ ID NO 23
<211> LENGTH: 7
<212> TYPE: PRT
<213> ORGANISM: Artificial Sequence
<220> FEATURE:
<223> OTHER INFORMATION: synthetic: designed sequence

<400> SEQUENCE: 23

Ala Ala Ser Asn Gln Gly Ser
1               5

<210> SEQ ID NO 24
<211> LENGTH: 9
<212> TYPE: PRT
<213> ORGANISM: Artificial Sequence
<220> FEATURE:
<223> OTHER INFORMATION: synthetic: designed sequence
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 24

Gln Gln Xaa Lys Glu Xaa Pro Xaa Thr
1               5

<210> SEQ ID NO 25
<211> LENGTH: 9
<212> TYPE: PRT
<213> ORGANISM: Artificial Sequence
<220> FEATURE:
<223> OTHER INFORMATION: synthetic: designed sequence

<400> SEQUENCE: 25

Gln Gln Ser Lys Glu Val Pro Trp Thr
1               5

<210> SEQ ID NO 26
<211> LENGTH: 9
<212> TYPE: PRT
<213> ORGANISM: Artificial Sequence
<220> FEATURE:
<223> OTHER INFORMATION: synthetic: designed sequence

<400> SEQUENCE: 26

Gln Gln Ser Lys Glu Val Pro Tyr Thr
1               5

<210> SEQ ID NO 27
<211> LENGTH: 9
<212> TYPE: PRT
<213> ORGANISM: Artificial Sequence
<220> FEATURE:
<223> OTHER INFORMATION: synthetic: designed sequence

<400> SEQUENCE: 27

Gln Gln Ser Lys Glu Ile Pro Trp Thr
```

-continued

```
1               5

<210> SEQ ID NO 28
<211> LENGTH: 9
<212> TYPE: PRT
<213> ORGANISM: Artificial Sequence
<220> FEATURE:
<223> OTHER INFORMATION: synthetic: designed sequence

<400> SEQUENCE: 28

Gln Gln Gly Lys Glu Val Pro Trp Thr
1               5

<210> SEQ ID NO 29
<211> LENGTH: 111
<212> TYPE: PRT
<213> ORGANISM: Mus musculus

<400> SEQUENCE: 29

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Phe
            20                  25                  30

Gly Ile Ser Phe Met Asn Trp Phe Gln Gln Lys Pro Gly Gln Pro Pro
        35                  40                  45

Lys Leu Leu Ile Tyr Val Ala Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Glu Asp Asp Thr Ala Met Tyr Phe Cys Gln Gln Ser Lys
                85                  90                  95

Glu Val Pro Trp Thr Phe Gly Gly Gly Thr Lys Leu Glu Ile Lys
            100                 105                 110

<210> SEQ ID NO 30
<211> LENGTH: 111
<212> TYPE: PRT
<213> ORGANISM: Mus musculus

<400> SEQUENCE: 30

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Gly Asn Phe
            20                  25                  30

Gly Ile Ser Phe Met Asn Trp Phe Gln Gln Lys Pro Gly Gln Pro Pro
        35                  40                  45

Lys Leu Leu Ile Tyr Thr Ala Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Glu Asp Asp Ser Ala Met Tyr Phe Cys Gln Gln Ser Lys
                85                  90                  95

Glu Val Pro Trp Thr Phe Gly Gly Gly Thr Lys Leu Glu Ile Lys
            100                 105                 110

<210> SEQ ID NO 31
<211> LENGTH: 111
<212> TYPE: PRT
<213> ORGANISM: Mus musculus
```

<400> SEQUENCE: 31

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Gly Asn Phe
            20                  25                  30

Gly Ile Ser Phe Met Asn Trp Phe Gln Gln Lys Pro Gly Gln Pro Pro
        35                  40                  45

Lys Leu Leu Ile Tyr Thr Ala Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Glu Asp Asp Ser Ala Met Tyr Phe Cys Gln Gln Ser Lys
                85                  90                  95

Glu Ile Pro Trp Thr Phe Gly Gly Gly Thr Lys Leu Glu Ile Lys
            100                 105                 110

<210> SEQ ID NO 32
<211> LENGTH: 111
<212> TYPE: PRT
<213> ORGANISM: Mus musculus

<400> SEQUENCE: 32

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val His Asn Phe
            20                  25                  30

Gly Ile Ser Phe Met Asn Trp Phe Gln Gln Lys Pro Gly Gln Pro Pro
        35                  40                  45

Lys Leu Leu Ile Tyr Thr Ala Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Val Glu Glu Asp Asp Thr Ala Met Tyr Phe Cys Gln Gln Gly Lys
                85                  90                  95

Glu Val Pro Trp Thr Phe Gly Gly Gly Thr Lys Leu Glu Ile Lys
            100                 105                 110

<210> SEQ ID NO 33
<211> LENGTH: 120
<212> TYPE: PRT
<213> ORGANISM: Mus musculus

<400> SEQUENCE: 33

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Glu Ile Arg Leu Lys Ser Asn Asn Tyr Ala Thr His Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Thr Arg Glu Asp Tyr Tyr Gly Tyr Pro Asp Tyr Trp Gly Gln

```
                100                 105                 110

Gly Thr Thr Leu Thr Val Ser Ser
        115                 120

<210> SEQ ID NO 34
<211> LENGTH: 119
<212> TYPE: PRT
<213> ORGANISM: Mus musculus

<400> SEQUENCE: 34

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Glu Ile Arg Leu Lys Ser Asn Lys Gly Ala Thr His Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Ala Ser Leu Leu Tyr Asp Gly Tyr Leu His Trp Gly Gln Gly
            100                 105                 110

Thr Leu Val Thr Val Ser Ala
        115

<210> SEQ ID NO 35
<211> LENGTH: 119
<212> TYPE: PRT
<213> ORGANISM: Mus musculus

<400> SEQUENCE: 35

Glu Val Lys Phe Glu Glu Ser Gly Gly Gly Leu Val Gln Pro Gly Gly
1               5                   10                  15

Ser Met Lys Leu Ser Cys Val Ala Ser Gly Phe Ser Phe Ser Asn Tyr
            20                  25                  30

Trp Met Asn Trp Val Arg Gln Ser Pro Glu Lys Gly Leu Glu Trp Val
        35                  40                  45

Ala Glu Ile Arg Leu Thr Ser Asn Lys Gln Ala Ile Tyr Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Ala Ser Leu Phe Tyr Asp Gly Tyr Leu His Trp Gly Gln Gly
            100                 105                 110

Thr Leu Val Thr Val Ser Ala
        115

<210> SEQ ID NO 36
<211> LENGTH: 120
<212> TYPE: PRT
<213> ORGANISM: Mus musculus

<400> SEQUENCE: 36

Glu Val Lys Leu Glu Glu Ser Gly Gly Gly Leu Val Gln Pro Gly Gly
1               5                   10                  15
```

```
Ser Met Lys Leu Ser Cys Ala Ala Ser Gly Phe Thr Phe Ser Asp Ala
            20                  25                  30

Trp Met Asp Trp Val Arg Gln Ser Pro Glu Lys Gly Leu Glu Trp Val
        35                  40                  45

Ala Glu Ile Arg Ser Lys Ala Asn Asn His Ala Thr Tyr Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Ser Leu Arg Ala Glu Asp Thr Gly Ile Tyr
                85                  90                  95

Tyr Cys Thr Thr Pro Thr Leu Tyr Gly Ala Met Asp Tyr Trp Gly Gln
            100                 105                 110

Gly Thr Ser Val Thr Val Ser Ala
            115                 120

<210> SEQ ID NO 37
<211> LENGTH: 649
<212> TYPE: PRT
<213> ORGANISM: Artificial Sequence
<220> FEATURE:
<223> OTHER INFORMATION: synthetic: (murine)Fc-(human)sIL6Ralpha-IL6

<400> SEQUENCE: 37

Glu Pro Arg Gly Pro Thr Ile Lys Pro Cys Pro Pro Cys Lys Cys Pro
1               5                   10                  15

Ala Pro Asn Leu Leu Gly Gly Pro Ser Val Phe Ile Phe Pro Pro Lys
            20                  25                  30

Ile Lys Asp Val Leu Met Ile Ser Leu Ser Pro Ile Val Thr Cys Val
            35                  40                  45

Val Val Asp Val Ser Glu Asp Asp Pro Asp Val Gln Ile Ser Trp Phe
        50                  55                  60

Val Asn Asn Val Glu Val His Thr Ala Gln Thr Gln Thr His Arg Glu
65                  70                  75                  80

Asp Tyr Asn Ser Thr Leu Arg Val Val Ser Ala Leu Pro Ile Gln His
                85                  90                  95

Gln Asp Trp Met Ser Gly Lys Glu Phe Lys Cys Lys Val Asn Asn Lys
            100                 105                 110

Asp Leu Pro Ala Pro Ile Glu Arg Thr Ile Ser Lys Pro Lys Gly Ser
            115                 120                 125

Val Arg Ala Pro Gln Val Tyr Val Leu Pro Pro Glu Glu Glu Met
        130                 135                 140

Thr Lys Lys Gln Val Thr Leu Thr Cys Met Val Thr Asp Phe Met Pro
145                 150                 155                 160

Glu Asp Ile Tyr Val Glu Trp Thr Asn Asn Gly Lys Thr Glu Leu Asn
                165                 170                 175

Tyr Lys Asn Thr Glu Pro Val Leu Asp Ser Asp Gly Ser Tyr Phe Met
            180                 185                 190

Tyr Ser Lys Leu Arg Val Glu Lys Lys Asn Trp Val Glu Arg Asn Ser
        195                 200                 205

Tyr Ser Cys Ser Val Val His Glu Gly Leu His Asn His His Thr Thr
    210                 215                 220

Lys Ser Phe Ser Arg Thr Pro Gly Ser Gly Asp Asp Asp Asp Lys
225                 230                 235                 240

Leu Pro Pro Glu Glu Pro Gln Leu Ser Cys Phe Arg Lys Ser Pro Leu
                245                 250                 255
```

```
Ser Asn Val Val Cys Glu Trp Gly Pro Arg Ser Thr Pro Ser Leu Thr
            260                 265                 270

Thr Lys Ala Val Leu Leu Val Arg Lys Phe Gln Asn Ser Pro Ala Glu
        275                 280                 285

Asp Phe Gln Glu Pro Cys Gln Tyr Ser Gln Glu Ser Gln Lys Phe Ser
    290                 295                 300

Cys Gln Leu Ala Val Pro Glu Gly Asp Ser Ser Phe Tyr Ile Val Ser
305                 310                 315                 320

Met Cys Val Ala Ser Ser Val Gly Ser Lys Phe Ser Lys Thr Gln Thr
                325                 330                 335

Phe Gln Gly Cys Gly Ile Leu Gln Pro Asp Pro Pro Ala Asn Ile Thr
            340                 345                 350

Val Thr Ala Val Ala Arg Asn Pro Arg Trp Leu Ser Val Thr Trp Gln
        355                 360                 365

Asp Pro His Ser Trp Asn Ser Ser Phe Tyr Arg Leu Arg Phe Glu Leu
    370                 375                 380

Arg Tyr Arg Ala Glu Arg Ser Lys Thr Phe Thr Thr Trp Met Val Lys
385                 390                 395                 400

Asp Leu Gln His His Cys Val Ile His Asp Ala Trp Ser Gly Leu Arg
                405                 410                 415

His Val Val Gln Leu Arg Ala Gln Glu Glu Phe Gly Gln Gly Glu Trp
            420                 425                 430

Ser Glu Trp Ser Pro Glu Ala Met Gly Thr Pro Trp Thr Glu Ser Arg
        435                 440                 445

Ser Pro Pro Ala Arg Gly Gly Gly Ser Gly Gly Gly Ser Val
    450                 455                 460

Glu Pro Val Pro Pro Gly Glu Asp Ser Lys Asp Val Ala Ala Pro His
465                 470                 475                 480

Arg Gln Pro Leu Thr Ser Ser Glu Arg Ile Asp Lys Gln Ile Arg Tyr
                485                 490                 495

Ile Leu Asp Gly Ile Ser Ala Leu Arg Lys Glu Thr Cys Asn Lys Ser
            500                 505                 510

Asn Met Cys Glu Ser Ser Lys Glu Ala Leu Ala Glu Asn Asn Leu Asn
        515                 520                 525

Leu Pro Lys Met Ala Glu Lys Asp Gly Cys Phe Gln Ser Gly Phe Asn
    530                 535                 540

Glu Glu Thr Cys Leu Val Lys Ile Ile Thr Gly Leu Leu Glu Phe Glu
545                 550                 555                 560

Val Tyr Leu Glu Tyr Leu Gln Asn Arg Phe Glu Ser Ser Glu Glu Gln
                565                 570                 575

Ala Arg Ala Val Gln Met Ser Thr Lys Val Leu Ile Gln Phe Leu Gln
            580                 585                 590

Lys Lys Ala Lys Asn Leu Asp Ala Ile Thr Thr Pro Asp Pro Thr Thr
        595                 600                 605

Asn Ala Ser Leu Leu Thr Lys Leu Gln Ala Gln Asn Gln Trp Leu Gln
    610                 615                 620

Asp Met Thr Thr His Leu Ile Leu Arg Ser Phe Lys Glu Phe Leu Gln
625                 630                 635                 640

Ser Ser Leu Arg Ala Leu Arg Gln Met
                645

<210> SEQ ID NO 38
<211> LENGTH: 1950
```

<212> TYPE: DNA
<213> ORGANISM: Artificial Sequence
<220> FEATURE:
<223> OTHER INFORMATION: synthetic: DNA encoding mature
(murine)Fc-(human)sIL6Ralpha-IL6

<400> SEQUENCE: 38

```
gagcccagag ggcccacaat caagccctgt cctccatgca aatgcccagc acctaacctc      60
ttgggtggac catccgtctt catcttccct ccaaagatca aggatgtact catgatctcc     120
ctgagcccca tagtcacatg tgtggtggtg gatgtgagcg aggatgaccc agatgtccag     180
atcagctggt ttgtgaacaa cgtggaagta cacacagctc agacacaaac ccatagagag     240
gattacaaca gtactctccg ggtggtcagt gccctcccca tccagcacca ggactggatg     300
agtggcaagg agttcaaatg caaggtcaac aacaaagacc tcccagcgcc catcgagaga     360
accatctcaa aacccaaagg tcagtaaga gctccacagg tatatgtctt gcctccacca     420
gaagaagaga tgactaagaa acaggtcact ctgacctgca tggtcacaga cttcatgcct     480
gaagacattt acgtggagtg gaccaacaac gggaaaacag agctaaacta caagaacact     540
gaaccagtcc tggactctga tggttcttac ttcatgtaca gcaagctgag agtggaaaag     600
aagaactggg tggaaagaaa tagctactcc tgttcagtgg tccacgaggg tctgcacaat     660
caccacacga ctaagagctt ctcccggacc ccggggttcag gggatgacga tgacgataag     720
cttccccccg aggagcccca gctctcctgc ttccggaaga gccccctcag caatgttgtt     780
tgtgagtggg gtcctcggag cacccccatcc ctgacgacaa aggctgtgct cttggtgagg     840
aagtttcaga acagtccggc cgaagacttc caggagccgt gccagtattc ccaggagtcc     900
cagaagttct cctgccagtt agcagtcccg gagggagaca gctctttcta catagtgtcc     960
atgtgcgtcg ccagtagtgt cgggagcaag ttcagcaaaa ctcaaacctt tcagggttgt    1020
ggaatcttgc agcctgatcc gcctgccaac atcacagtca ctgccgtggc cagaaacccc    1080
cgctggctca gtgtcacctg caaggaccccc cactcctgga actcatcttt ctacagacta    1140
cggtttgagc tcagatatcg ggctgaacgg tcaaagacat tcacaacatg gatggtcaag    1200
gacctccagc atcactgtgt catccacgac gcctggagcg gcctgaggca cgtggtgcag    1260
cttcgtgccc aggaggagtt cgggcaaggc gagtggagcg agtggagccc ggaggccatg    1320
ggcacgcctt ggacagaatc caggagtcct ccagctagag ggggcggggg cagtgggggc    1380
gggggcagtg tagaaccggt accccccagga gaagattcca agatgtgagc tgccccacac    1440
agacagccac tcacctcttc agaacgaatt gacaaacaaa ttcggtacat cctcgacggc    1500
atctcagccc tgagaaagga gacatgtaac aagagtaaca tgtgtgaaag cagcaaagag    1560
gcactggcag aaaacaacct gaaccttcca agatggctg aaaaagatgg atgcttccaa    1620
tctggattca atgaggagac ttgcctggtg aaaatcatca ctggtctttt ggagtttgag    1680
gtatacctag agtacctcca gaacagattt gagagtagtg aggaacaagc cagagctgtg    1740
cagatgagta caaaagtcct gatccagttc ctgcagaaaa aggcaaagaa tctagatgca    1800
ataaccaccc ctgacccaac cacaaatgcc agcctgctga cgaagctgca ggcacagaac    1860
cagtggctgc aggacatgac aactcatctc attctgcgca gctttaagga gttcctgcag    1920
tccagcctga ggctcttcg gcaaatgtag                                     1950
```

<210> SEQ ID NO 39
<211> LENGTH: 452
<212> TYPE: PRT
<213> ORGANISM: Artificial Sequence

```
<220> FEATURE:
<223> OTHER INFORMATION: synthetic: mature (murine)Fc-(human)sIL6Ralpha

<400> SEQUENCE: 39

Glu Pro Arg Gly Pro Thr Ile Lys Pro Cys Pro Pro Cys Lys Cys Pro
1               5                   10                  15

Ala Pro Asn Leu Leu Gly Gly Pro Ser Val Phe Ile Phe Pro Pro Lys
            20                  25                  30

Ile Lys Asp Val Leu Met Ile Ser Leu Ser Pro Ile Val Thr Cys Val
        35                  40                  45

Val Val Asp Val Ser Glu Asp Asp Pro Asp Val Gln Ile Ser Trp Phe
    50                  55                  60

Val Asn Asn Val Glu Val His Thr Ala Gln Thr Gln Thr His Arg Glu
65                  70                  75                  80

Asp Tyr Asn Ser Thr Leu Arg Val Val Ser Ala Leu Pro Ile Gln His
                85                  90                  95

Gln Asp Trp Met Ser Gly Lys Glu Phe Lys Cys Lys Val Asn Asn Lys
            100                 105                 110

Asp Leu Pro Ala Pro Ile Glu Arg Thr Ile Ser Lys Pro Lys Gly Ser
        115                 120                 125

Val Arg Ala Pro Gln Val Tyr Val Leu Pro Pro Glu Glu Glu Met
    130                 135                 140

Thr Lys Lys Gln Val Thr Leu Thr Cys Met Val Thr Asp Phe Met Pro
145                 150                 155                 160

Glu Asp Ile Tyr Val Glu Trp Thr Asn Asn Gly Lys Thr Glu Leu Asn
                165                 170                 175

Tyr Lys Asn Thr Glu Pro Val Leu Asp Ser Asp Gly Ser Tyr Phe Met
            180                 185                 190

Tyr Ser Lys Leu Arg Val Glu Lys Lys Asn Trp Val Glu Arg Asn Ser
        195                 200                 205

Tyr Ser Cys Ser Val Val His Glu Gly Leu His Asn His His Thr Thr
    210                 215                 220

Lys Ser Phe Ser Arg Thr Pro Gly Ser Gly Asp Asp Asp Asp Lys
225                 230                 235                 240

Leu Pro Pro Glu Glu Pro Gln Leu Ser Cys Phe Arg Lys Ser Pro Leu
                245                 250                 255

Ser Asn Val Val Cys Glu Trp Gly Pro Arg Ser Thr Pro Ser Leu Thr
            260                 265                 270

Thr Lys Ala Val Leu Leu Val Arg Lys Phe Gln Asn Ser Pro Ala Glu
        275                 280                 285

Asp Phe Gln Glu Pro Cys Gln Tyr Ser Gln Glu Ser Gln Lys Phe Ser
    290                 295                 300

Cys Gln Leu Ala Val Pro Glu Gly Asp Ser Ser Phe Tyr Ile Val Ser
305                 310                 315                 320

Met Cys Val Ala Ser Ser Val Gly Ser Lys Phe Ser Lys Thr Gln Thr
                325                 330                 335

Phe Gln Gly Cys Gly Ile Leu Gln Pro Asp Pro Pro Ala Asn Ile Thr
            340                 345                 350

Val Thr Ala Val Ala Arg Asn Pro Arg Trp Leu Ser Val Thr Trp Gln
        355                 360                 365

Asp Pro His Ser Trp Asn Ser Ser Phe Tyr Arg Leu Arg Phe Glu Leu
    370                 375                 380

Arg Tyr Arg Ala Glu Arg Ser Lys Thr Phe Thr Thr Trp Met Val Lys
385                 390                 395                 400
```

```
Asp Leu Gln His His Cys Val Ile His Asp Ala Trp Ser Gly Leu Arg
                405                 410                 415
His Val Val Gln Leu Arg Ala Gln Glu Glu Phe Gly Gln Gly Glu Trp
            420                 425                 430
Ser Glu Trp Ser Pro Glu Ala Met Gly Thr Pro Trp Thr Glu Ser Arg
        435                 440                 445
Ser Pro Pro Ala
        450
```

<210> SEQ ID NO 40
<211> LENGTH: 1359
<212> TYPE: DNA
<213> ORGANISM: Artificial Sequence
<220> FEATURE:
<223> OTHER INFORMATION: synthetic: DNA encoding mature
      (murine)Fc-(human)sIL6Ralpha

<400> SEQUENCE: 40

```
gagcccagag ggcccacaat caagccctgt cctccatgca aatgcccagc acctaacctc     60
ttgggtggac catccgtctt catcttccct ccaaagatca aggatgtact catgatctcc    120
ctgagcccca tagtcacatg tgtggtggtg gatgtgagcg aggatgaccc agatgtccag    180
atcagctggt ttgtgaacaa cgtggaagta cacacagctc agacacaaac ccatagagag    240
gattacaaca gtactctccg ggtggtcagt gccctcccca tccagcacca ggactggatg    300
agtggcaagg agttcaaatg caaggtcaac aacaaagacc tcccagcgcc catcgagaga    360
accatctcaa acccaaagg gtcagtaaga gctccacagg tatatgtctt gcctccacca    420
gaagaagaga tgactaagaa acaggtcact ctgacctgca tggtcacaga cttcatgcct    480
gaagacattt acgtggagtg gaccaacaac gggaaaacag agctaaacta caagaacact    540
gaaccagtcc tggactctga tggttcttac ttcatgtaca gcaagctgag agtggaaaag    600
aagaactggg tggaaagaaa tagctactcc tgttcagtgg tccacgaggg tctgcacaat    660
caccacacga ctaagagctt ctcccggacc ccgggttcag gggatgacga tgacgataag    720
cttccccccg aggagcccca gctctcctgc ttccggaaga gccccctcag caatgttgtt    780
tgtgagtggg gtcctcggag caccccatcc ctgacgacaa aggctgtgct cttggtgagg    840
aagtttcaga cagtccggc cgaagacttc aggagccgt gccagtattc ccaggagtcc    900
cagaagttct cctgccagtt agcagtcccg gagggagaca gctctttcta catagtgtcc    960
atgtgcgtcg ccagtagtgt cgggagcaag ttcagcaaaa ctcaaacctt tcagggttgt   1020
ggaatcttgc agcctgatcc gcctgccaac atcacagtca ctgccgtggc cagaaacccc   1080
cgctggctca gtgtcacctg caagacccc cactcctgga actcatcttt ctacagacta   1140
cggtttgagc tcagatatcg ggctgaacgg tcaaagacat tcacaacatg gatggtcaag   1200
gacctccagc atcactgtgt catccacgac gcctggagcg gcctgaggca cgtggtgcag   1260
cttcgtgccc aggaggagtt cgggcaaggc gagtggagcg agtggagccc ggaggccatg   1320
ggcacgcctt ggacagaatc caggagtcct ccagcttag                          1359
```

<210> SEQ ID NO 41
<211> LENGTH: 412
<212> TYPE: PRT
<213> ORGANISM: Artificial Sequence
<220> FEATURE:
<223> OTHER INFORMATION: synthetic: mature (murine)Fc-(human)IL6

<400> SEQUENCE: 41

```
Glu Pro Arg Gly Pro Thr Ile Lys Pro Cys Pro Pro Cys Lys Cys Pro
1               5                   10                  15

Ala Pro Asn Leu Leu Gly Gly Pro Ser Val Phe Ile Phe Pro Pro Lys
            20                  25                  30

Ile Lys Asp Val Leu Met Ile Ser Leu Ser Pro Ile Val Thr Cys Val
            35                  40                  45

Val Val Asp Val Ser Glu Asp Pro Asp Val Gln Ile Ser Trp Phe
50                  55                  60

Val Asn Asn Val Glu Val His Thr Ala Gln Thr Gln Thr His Arg Glu
65                  70                  75                  80

Asp Tyr Asn Ser Thr Leu Arg Val Val Ser Ala Leu Pro Ile Gln His
                85                  90                  95

Gln Asp Trp Met Ser Gly Lys Glu Phe Lys Cys Lys Val Asn Asn Lys
            100                 105                 110

Asp Leu Pro Ala Pro Ile Glu Arg Thr Ile Ser Lys Pro Lys Gly Ser
            115                 120                 125

Val Arg Ala Pro Gln Val Tyr Val Leu Pro Pro Glu Glu Glu Met
130                 135                 140

Thr Lys Lys Gln Val Thr Leu Thr Cys Met Val Thr Asp Phe Met Pro
145                 150                 155                 160

Glu Asp Ile Tyr Val Glu Trp Thr Asn Asn Gly Lys Thr Glu Leu Asn
                165                 170                 175

Tyr Lys Asn Thr Glu Pro Val Leu Asp Ser Asp Gly Ser Tyr Phe Met
            180                 185                 190

Tyr Ser Lys Leu Arg Val Glu Lys Lys Asn Trp Val Glu Arg Asn Ser
            195                 200                 205

Tyr Ser Cys Ser Val Val His Glu Gly Leu His Asn His His Thr Thr
            210                 215                 220

Lys Ser Phe Ser Arg Thr Pro Gly Lys Glu Asp Ser Lys Asp Val Ala
225                 230                 235                 240

Ala Pro His Arg Gln Pro Leu Thr Ser Ser Glu Arg Ile Asp Lys Gln
            245                 250                 255

Ile Arg Tyr Ile Leu Asp Gly Ile Ser Ala Leu Arg Lys Glu Thr Cys
            260                 265                 270

Asn Lys Ser Asn Met Cys Glu Ser Ser Lys Glu Ala Leu Ala Glu Asn
            275                 280                 285

Asn Leu Asn Leu Pro Lys Met Ala Glu Lys Asp Gly Cys Phe Gln Ser
            290                 295                 300

Gly Phe Asn Glu Glu Thr Cys Leu Val Lys Ile Ile Thr Gly Leu Leu
305                 310                 315                 320

Glu Phe Glu Val Tyr Leu Glu Tyr Leu Gln Asn Arg Phe Glu Ser Ser
                325                 330                 335

Glu Glu Gln Ala Arg Ala Val Gln Met Ser Thr Lys Val Leu Ile Gln
            340                 345                 350

Phe Leu Gln Lys Lys Ala Lys Asn Leu Asp Ala Ile Thr Thr Pro Asp
            355                 360                 365

Pro Thr Thr Asn Ala Ser Leu Leu Thr Lys Leu Gln Ala Gln Asn Gln
            370                 375                 380

Trp Leu Gln Asp Met Thr Thr His Leu Ile Leu Arg Ser Phe Lys Glu
385                 390                 395                 400

Phe Leu Gln Ser Ser Leu Arg Ala Leu Arg Gln Met
                405                 410
```

```
<210> SEQ ID NO 42
<211> LENGTH: 1239
<212> TYPE: DNA
<213> ORGANISM: Artificial Sequence
<220> FEATURE:
<223> OTHER INFORMATION: synthetic: DNA encoding mature
      (murine)Fc-(human)IL6

<400> SEQUENCE: 42
gagcccagag ggcccacaat caagccctgt cctccatgca aatgcccagc acctaacctc      60
ttgggtggac catccgtctt catcttccct ccaaagatca aggatgtact catgatctcc     120
ctgagcccca tagtcacatg tgtggtggtg gatgtgagcg aggatgaccc agatgtccag     180
atcagctggt ttgtgaacaa cgtggaagta cacacagctc agacacaaac ccatagagag     240
gattacaaca gtactctccg ggtggtcagt gccctcccca tccagcacca ggactggatg     300
agtggcaagg agttcaaatg caaggtcaac aacaaagacc tcccagcgcc catcgagaga     360
accatctcaa acccaaagg gtcagtaaga gctccacagg tatatgtctt gcctccacca     420
gaagaagaga tgactaagaa acaggtcact ctgacctgca tggtcacaga cttcatgcct     480
gaagacattt acgtggagtg gaccaacaac gggaaaacag agctaaacta caagaacact     540
gaaccagtcc tggactctga tggttcttac ttcatgtaca gcaagctgag agtggaaaag     600
aagaactggg tggaaagaaa tagctactcc tgttcagtgg tccacgaggg tctgcacaat     660
caccacacga ctaagagctt ctcccggacc ccgggtaaag aagattccaa agatgtagct     720
gccccacaca gacagccact cacctcttca gaacgaattg acaaacaaat tcggtacatc     780
ctcgacggca tctcagccct gagaaaggag acatgtaaca gagtaacat gtgtgaaagc     840 agcaaagagg cactggcaga aaacaacctg aaccttccaa agatggctga aaaagatgga     900
tgcttccaat ctggattcaa tgaggagact tgcctggtga aaatcatcac tggtctttg      960 gagtttgagg tatacctaga gtacctccag aacagatttg agagtagtga ggaacaagcc    1020
agagctgtgc agatgagtac aaaagtcctg atccagttcc tgcagaaaaa ggcaaagaat    1080
ctagatgcaa taaccacccc tgacccaacc acaaatgcca gcctgctgac gaagctgcag    1140
gcacagaacc agtggctgca ggacatgaca actcatctca ttctgcgcag ctttaaggag    1200
ttcctgcagt ccagcctgag ggctcttcgg caaatgtag                           1239

<210> SEQ ID NO 43
<211> LENGTH: 18
<212> TYPE: DNA
<213> ORGANISM: Artificial Sequence
<220> FEATURE:
<223> OTHER INFORMATION: synthetic: VH amplification PCR#1 5'
      oligonucleotide #1

<400> SEQUENCE: 43
acaacgcaga gtacgcgg                                                    18

<210> SEQ ID NO 44
<211> LENGTH: 20
<212> TYPE: DNA
<213> ORGANISM: Artificial Sequence
<220> FEATURE:
<223> OTHER INFORMATION: synthetic: VH amplification PCR#1 3'
      oligonucleotide #1

<400> SEQUENCE: 44
aggagagctg ggaaggtgtg                                                  20
```

<210> SEQ ID NO 45
<211> LENGTH: 18
<212> TYPE: DNA
<213> ORGANISM: Artificial Sequence
<220> FEATURE:
<223> OTHER INFORMATION: synthetic: VH amplification PCR#2 5'
      oligonucleotide #2

<400> SEQUENCE: 45
acaacgcaga gtacgcgg                                                18

<210> SEQ ID NO 46
<211> LENGTH: 21
<212> TYPE: DNA
<213> ORGANISM: Artificial Sequence
<220> FEATURE:
<223> OTHER INFORMATION: synthetic: VH amplification PCR#2 3'
      oligonucleotide #2

<400> SEQUENCE: 46
tagcccttga ccaggcatcc c                                            21

<210> SEQ ID NO 47
<211> LENGTH: 18
<212> TYPE: DNA
<213> ORGANISM: Artificial Sequence
<220> FEATURE:
<223> OTHER INFORMATION: synthetic: VK amplification PCR#1 5'
      oligonucleotide #1

<400> SEQUENCE: 47
acaacgcaga gtacgcgg                                                18

<210> SEQ ID NO 48
<211> LENGTH: 23
<212> TYPE: DNA
<213> ORGANISM: Artificial Sequence
<220> FEATURE:
<223> OTHER INFORMATION: synthetic: VK amplification PCR#1 3'
      oligonucleotide #1

<400> SEQUENCE: 48
ctgccatcaa tcttccactt gac                                          23

<210> SEQ ID NO 49
<211> LENGTH: 20
<212> TYPE: DNA
<213> ORGANISM: Artificial Sequence
<220> FEATURE:
<223> OTHER INFORMATION: synthetic: VK amplification PCR#2 5'
      oligonucleotide #2

<400> SEQUENCE: 49
catcctctct tccagctctc                                              20

<210> SEQ ID NO 50
<211> LENGTH: 18
<212> TYPE: DNA
<213> ORGANISM: Artificial Sequence
<220> FEATURE:
<223> OTHER INFORMATION: synthetic: VK amplification PCR#2 3'
      oligonucleotide #2

<400> SEQUENCE: 50
ctgaggcacc tccagatg                                                18

```
<210> SEQ ID NO 51
<211> LENGTH: 360
<212> TYPE: DNA
<213> ORGANISM: Mus musculus

<400> SEQUENCE: 51
gaagtgaagc ttgaggagtc tggaggaggc ttggtgcaac ctggaggatc catgaaactc      60
tcctgtgttg cctctggatt cactttcagt aactactgga tgaactgggt ccgccagtct     120
ccagagaagg ggcttgagtg ggttgctgaa attagattga atctaataa ttatgcaaca      180 cattatgcgg agtctgtgaa agggaggttc accatctcaa gagatgattc caaaagtagt     240
gtctacctgc aaatgaacaa cttaagagct gaagacactg gcatttatta ctgtaccagg     300
gaggactact acggctaccc tgactactgg ggccaaggca ccactctcac agtctcctca     360

<210> SEQ ID NO 52
<211> LENGTH: 333
<212> TYPE: DNA
<213> ORGANISM: Mus musculus

<400> SEQUENCE: 52
gacattgtgc tgacccagtc tccagcttct ttggctgtgt ctctaggtca gagggccacc      60
atctcctgca gagccagcga aagtgttgat aattttggca ttagttttat gaactggttc     120
caacagaaac ctggacagcc acccaaactc ctcatctatg ttgcatccaa ccaaggatcc     180
ggggtccctg ccaggtttag tggcagtggg tctgggacag acttcagcct caacatccat     240
cctatggagg aggatgatac tgcaatgtat ttctgtcagc aaagtaagga ggttccgtgg     300
acgttcggtg gaggcaccaa gctggaaatc aaa                                   333

<210> SEQ ID NO 53
<211> LENGTH: 357
<212> TYPE: DNA
<213> ORGANISM: Mus musculus

<400> SEQUENCE: 53
gaagtgaaac ttgaggagtc tggaggaggc ttggttcaac ctggaggatc catgaaactc      60
tcctgtgttg cctctggatt cactttcagt aactactgga tgaactgggt ccgccagtct     120
ccagagaagg ggcttgagtg ggttgctgaa attagactga atctaataa gggtgcaaca      180 cattatgcgg agtctgtgaa agggaggttc accatctcaa gggatgattc caaaagtagt     240
gtctacctgc aaatgaacaa cttaagagct gaagacactg gcatttatta ctgtgccagc     300
cttttgtatg atggttactt acattggggc caagggactc tggtcactgt ctctgca       357

<210> SEQ ID NO 54
<211> LENGTH: 333
<212> TYPE: DNA
<213> ORGANISM: Mus musculus

<400> SEQUENCE: 54
gacattgtgc tgacccaatc tccagcttct ttggctgtgt ctctagggca gagggccacc      60
atctcctgca gagccagcga aagtgttggt aattttggca ttagttttat gaattggttc     120
caacagaaac caggacagcc acccaaactc ctcatctata ctgcatccaa ccaaggatcc     180
ggggtccctg ccaggtttag tggcagtggg tctgggacag acttcagcct caacatccat     240
cctatggagg aggatgattc tgcaatgtat ttctgtcagc aaagtaagga ggttccgtgg     300
acgttcggtg gaggcaccaa actggaaatc aaa                                   333
```

<210> SEQ ID NO 55
<211> LENGTH: 357
<212> TYPE: DNA
<213> ORGANISM: Mus musculus

<400> SEQUENCE: 55

```
gaagtgaagt tgaggagtc tggaggaggc ttggtgcaac cgggaggatc catgaaactc      60
tcctgtgttg cctctggatt cagtttcagt aactactgga tgaactgggt ccgccagtct    120
ccagagaagg ggcttgagtg ggttgctgaa attagattga catctaataa gcaggcaata    180
tattatgcgg agtctgtgaa agggagattc accatctcaa gagatgattc caaaagtagt    240
gtctacctgc aaatgaacaa cctaagagct gaagacactg gcatttatta ctgtgccagc    300
cttttctatg atggttactt acattggggc caagggactc tggtcactgt ctctgca       357
```

<210> SEQ ID NO 56
<211> LENGTH: 333
<212> TYPE: DNA
<213> ORGANISM: Mus musculus

<400> SEQUENCE: 56

```
gacattgtgc tgacccaatc tccagcttct ttggctgtgt ctctagggca gagggccacc     60
atctcctgca gagccagcga agtgttggt aattttggca ttagttttat gaactggttc    120
caacagaaac caggacagcc acccaaactc ctcatctata ctgcatccaa ccaaggatcc    180
ggggtccctg ccaggtttag tggcagtggg tctgggacag acttcagcct caacatccat    240
cctatggagg aggatgattc tgcaatgtat ttctgtcagc aaagtaagga gattccgtgg    300
acgttcggtg aggcaccaa actggaaatc aaa                                  333
```

<210> SEQ ID NO 57
<211> LENGTH: 360
<212> TYPE: DNA
<213> ORGANISM: Mus musculus

<400> SEQUENCE: 57

```
gaagtgaagc ttgaggagtc tggaggaggc ttggtgcaac ctggaggatc catgaaactc      60
tcttgtgctg cctctggatt cactttagt gacgcctgga tggactgggt ccgccagtct    120
ccagagaagg ggcttgagtg ggttgctgaa attagaagta aagctaataa tcatgcaaca    180
tactatgctg agtctgtgaa agggaggttc accatctcaa gagatgattc caaaagtagt    240
gtctacctgc aaatgaacag cctaagagct gaagacactg gcatttatta ctgtacgacc    300
cctactctct atggcgctat ggactactgg ggtcaaggaa cctcagtcac cgtctctgca    360
```

<210> SEQ ID NO 58
<211> LENGTH: 334
<212> TYPE: DNA
<213> ORGANISM: Mus musculus

<400> SEQUENCE: 58

```
gacattgtgc tgacccaatc tccagcttct ttggctgtgt ctcttgggca gagggccacc     60
atctcctgca gagccagcga agtgttcat aattttggca ttagctttat gaactggttc    120
caacagaaac caggacagcc acccaaactc ctcatctata ctgcatccaa ccaaggatcc    180
ggggtccctg ccaggtttag tggcagtggg tctgggacag acttcagcct caacatccat    240
cctgtggaag aggatgatac tgcaatgtat ttctgtcaac aagtaagga ggttccgtgg     300
acgttcggtg aggcaccaa gctggaaatc aaac                                 334
```

```
<210> SEQ ID NO 59
<211> LENGTH: 27
<212> TYPE: DNA
<213> ORGANISM: Artificial Sequence
<220> FEATURE:
<223> OTHER INFORMATION: synthetic: VL forward primer (with Afl II
      site): 4447s

<400> SEQUENCE: 59
cttaagcgac attgtgctga cccaatc                                           27

<210> SEQ ID NO 60
<211> LENGTH: 34
<212> TYPE: DNA
<213> ORGANISM: Artificial Sequence
<220> FEATURE:
<223> OTHER INFORMATION: synthetic: VL reverse primer (with Bgl II
      site): 5225a

<400> SEQUENCE: 60
agatctactt acgtttgatt tccagtttgg tgcc                                   34

<210> SEQ ID NO 61
<211> LENGTH: 27
<212> TYPE: DNA
<213> ORGANISM: Artificial Sequence
<220> FEATURE:
<223> OTHER INFORMATION: synthetic: VH forward primer (with Afl II
      site): 5226s

<400> SEQUENCE: 61
cttaagcgaa gtgaagtttg aggagtc                                           27

<210> SEQ ID NO 62
<211> LENGTH: 31
<212> TYPE: DNA
<213> ORGANISM: Artificial Sequence
<220> FEATURE:
<223> OTHER INFORMATION: synthetic: VH reverse primer (with Hind III
      site): 5227a

<400> SEQUENCE: 62
aagcttactt acctgcagag acagtgacca g                                      31
```

METHODS OF TREATING CANCER COMPRISING ADMINISTERING AN INTERLEUKIN-6 ANTIBODY VARIABLE REGION

CROSS-REFERENCE TO RELATED APPLICATIONS

This application claims priority to and the benefit of U.S. Provisional Patent Application No. 60/755,383, filed on Dec. 30, 2005, the entire contents of which are incorporated by reference herein.

FIELD OF THE INVENTION

This invention relates to antagonists of interleukin-6 (IL-6) that are useful in suppressing IL-6 signaling pathway and in treating IL-6 related diseases. In particular, this invention relates to IL-6 antagonists that block the interaction between IL-6 and gp130.

BACKGROUND OF THE INVENTION

Interleukin-6 (IL-6) is involved in several diseases, including many cancers and autoimmune diseases. Interleukin-6 is secreted by many advanced cancers, such as hormone-independent prostate cancer, and is believed to be a growth factor for such cancers. In addition, the secretion of IL-6 by cancer cells is believed to cause cachexia, the wasting syndrome characteristic of advanced cancers. Therefore, inhibition of IL-6 action would be useful in treatment of such cancers.

IL-6 also plays a key role in B cell development. Autoimmune diseases with a significant antibody component, such as rheumatoid arthritis, could be treated by inhibition of IL-6. Disorders involving proliferation of B cells, such as multiple myeloma and B cell lymphoma, could also be treated by inhibition of IL-6 activity.

In addition, IL-6 plays an important role in bone remodeling by promoting bone resorption. Inhibitors of IL-6 activity would have the effect of reducing bone resorption and could be used to treat osteoporosis.

When IL-6 is produced as part of a disease or disorder, it is often complexed with a soluble IL-6Ralpha subunit and is often secreted from cells in the form of such a complex. As a result, it is often not useful to treat a patient with an antibody or other inhibitor that blocks the interaction between IL-6 and IL-6Ralpha, because such an antibody or inhibitor can have no effect on a pre-formed complex. Therefore, there is a need in the art for improved treatment of IL-6-mediated diseases.

SUMMARY OF THE INVENTION

The present invention provides improved compositions and methods for treatment of IL-6-mediated diseases, in particular, cancers and autoimmune diseases that involve IL-6 over activation. Specifically, the present invention provides a novel IL-6 antagonist that effectively blocks the interaction between IL-6 and gp130, in particular, an IL-6 antagonist that prevents the pre-formed IL-6 and IL-6Ralpha complex from binding to gp130. In addition, the present invention provides methods of generating a novel IL-6 antagonist that blocks the interaction between IL-6 and gp130.

Thus, in one aspect, the present invention provides an isolated IL-6 antagonist that prevents IL-6 complexed with IL-6Ralpha from binding to gp130. In one embodiment, the isolated IL-6 antagonist contains an antibody variable region and an Fc region derived from a human antibody. In alternative embodiments, the Fc region suitable for the invention may be derived from an antibody obtained from a mouse, a rat, a cow, a dog, a chicken, a horse, a fish, a monkey, or other non-human species. In a preferred embodiment, the antibody variable region binds to a region on IL-6 such that the binding sterically blocks the interaction between IL-6 and gp130.

In some embodiments, the invention provides an isolated IL-6 antagonist comprising an antibody variable region that includes a heavy chain CDR1 containing the amino acid sequence $FX_1FSX_2X_3WMX_4$ (SEQ ID NO:1). $X_1$, $X_2$, $X_3$ or $X_4$ may be any amino acid. Preferably, $X_1$ is Thr, Ser, Ala or Cys; $X_2$ is Asn or Asp; $X_3$ is Tyr or Ala; and $X_4$ is Asn or Asp. In particular, the heavy chain CDR1 may contain one of the following amino acid sequences: FTFSNYWMN (SEQ ID NO:2), FSFSNYWMN (SEQ ID NO:3), or FTFSDAWMD (SEQ ID NO:4).

In some embodiments, the invention provides an isolated IL-6 antagonist comprising an antibody variable region that includes a heavy chain CDR2 containing the amino acid sequence $EIRX_1X_2X_3NX_4X_5AX_6X_7YAESVKG$ (SEQ ID NO:5). $X_1$, $X_2$, $X_3$, $X_4$, $X_5$, $X_6$ or $X_7$ may be any amino acid. Preferably, $X_1$ is Leu or Ser; $X_2$ is Lys or Thr; $X_3$ is Ser or Ala; $X_4$ is Asn or Lys; $X_5$ is Tyr, Gly, Gln or His; $X_6$ is Thr or Ile; and $X_7$ is His or Tyr. In particular, the antibody variable region includes a heavy chain CDR2 containing one of the following amino acid sequences: EIRLKSNNYATHYAESVKG (SEQ ID NO:6), EIRLKSNKGATHYAESVKG (SEQ ID NO:7), EIRLTSNKQAIYYAESVKG (SEQ ID NO:8), or EIRSKANNHATYYAESVKG (SEQ ID NO:9).

In some embodiments, the invention provides an isolated IL-6 antagonist comprising an antibody variable region that includes a heavy chain CDR3 containing the amino acid sequence $X_1X_2X_3X_4GX_5X_6X_7X_8$ (SEQ ID NO: 10). $X_1$, $X_2$, $X_3$, $X_4$, $X_5$, $X_6$, $X_7$ or $X_8$ may be any amino acid or a peptide bond. Preferably, $X_1$ is Glu, Leu or Pro; $X_2$ is Asp, Leu, Phe or Thr; X3 is Tyr or Leu; $X_4$ is Tyr or Asp; $X_5$ is Tyr or Ala; $X_6$ is Pro, Met or a peptide bond; $X_7$ is Asp or Leu; and $X_8$ is Tyr or His. In particular, the antibody variable region includes a heavy chain CDR3 containing one of the following amino acid sequences: EDYYGYPDY (SEQ ID NO:11), LLYDGYLH (SEQ ID NO:12), LFYDGYLH (SEQ ID NO:13), or PTLYGAMDY (SEQ ID NO:14).

In some embodiments, the invention provides an isolated IL-6 antagonist comprising an antibody variable region that includes a light chain CDR1 containing the amino acid sequence RASESVX1NX2GISFM (SEQ ID NO: 15). X1 or X2 may be any amino acid. Preferably, X1 is Asp, Gly or His; and X2 is Phe or Tyr. In particular, the antibody variable region includes a light chain CDR1 containing one of the following amino acid sequences:

```
RASESVDNFGISFM,      (SEQ ID NO:16)

RASESVGNFGISFM,      (SEQ ID NO:17)

RASESVHNFGISFM,      (SEQ ID NO:18)

or

RASESVDNYGISFM.      (SEQ ID NO:19)
```

In some embodiments, the invention provides an isolated IL-6 antagonist comprising an antibody variable region that includes a light chain CDR2 containing the amino acid sequence XASNQGS (SEQ ID NO:20). X may be any amino acid. Preferably, X is Ala, Val or Thr. In particular, the antibody variable region includes a light chain CDR2 containing one of the following amino acid sequences: TASNQGS (SEQ ID NO:21), VASNQGS (SEQ ID NO:22), or AASNQGS (SEQ ID NO:23).

In some embodiments, the invention provides an isolated IL-6 antagonist comprising an antibody variable region that includes a light chain CDR3 containing the amino acid sequence $QQX_1KEX_2PX_3T$ (SEQ ID NO:24). $X_1$, $X_2$ or $X_3$ may be any amino acid. Preferably, $X_1$ is Ser or Gly; $X_2$ is Val or Ile; and $X_3$ is Trp or Tyr. In particular, the antibody variable region includes a light chain CDR3 containing one of the following amino acid sequences: QQSKEVPWT (SEQ ID NO:25), QQSKEVPYT (SEQ ID NO:26), QQSKEIPWT (SEQ ID NO:27), or QQGKEVPWT (SEQ ID NO:28).

In a preferred embodiment, the IL-6 antagonist of the present invention is an antibody or a fragment thereof.

In some embodiments, the antibody includes a light chain containing one of the following amino acid sequences: SEQ ID NO:29, SEQ ID NO:30, SEQ ID NO:31, or SEQ ID NO:32. Alternatively, the antibody includes a light chain containing an amino acid sequence at least 60%, 65%, 70%, 75%, 80%, 85%, 90%, or 95% identical to any one of the above-identified sequences, for example, SEQ ID NO:31 (Mab#471).

In other embodiments, the antibody includes a heavy chain containing one of the following amino acid sequences: SEQ ID NO:33, SEQ ID NO:34, SEQ ID NO:35, or SEQ ID NO:36. Alternatively, the antibody includes a heavy chain containing an amino acid sequence at least 60%, 65%, 70%, 75%, 80%, 85%, 90%, or 95% identical to any one of the above-identified sequences, for example, SEQ ID NO:35 (Mab#471).

The present invention also provides nucleic acids encoding the IL-6 antagonist as described in various embodiments above. In particular, the present invention provides nucleic acids encoding the light chain and/or the heavy chain of the anti-IL-6 antibodies described above.

In another aspect, the present invention provides an isolated IL-6 antagonist including an antibody variable region that binds to an epitope on IL-6 containing an amino acid selected from the group consisting of Leu19, Arg24, Lys27, Arg30, Tyr31, Asp34 and Trp157 such that the binding sterically blocks the interaction between IL-6 and gp130.

Typically, the IL-6 antagonist includes an Fc moiety. Preferably, the Fc moiety is derived from a human antibody. In a more preferred embodiment, all of the constant regions in the IL-6 antagonist of the invention are derived from a human antibody. In alternative embodiments, the Fc region suitable for the invention may be derived from an antibody obtained from a mouse, a rat, a cow, a dog, a chicken, a horse, a fish, a monkey, or other non-human species.

In another aspect, the present invention provides a method for treating a disease in a subject by administering to the subject the isolated IL-6 antagonist of the invention as described above. Specifically, the present invention provides a method for treating a disease or a symptom in a subject by administering a protein including an antibody V region that binds to IL-6 and sterically blocks its interaction with gp130. Such proteins include, but are not limited to, antibodies, antibody fragments that lack various constant regions, minibodies, scFv proteins, antibody fusion proteins. Preferably, the antibody V region that binds to IL-6 and sterically blocks its interaction with gp130 does not sterically block the interaction between IL-6 and the IL-6 receptor alpha subunit. The method of the present invention is particularly useful in treating diseases, disorders, and side effects that involve IL-6, such as, for example, autoimmune diseases including, but not limited to, rheumatoid arthritis, Sjogren's syndrome, multiple sclerosis, systemic lupus erythematosus, Graves' disease, Hashimoto's disease, and Castleman's disease, acute and chronic inflammation, and osteoporosis and other disorders involving loss of bone mass, and cancers including, but not limited to, hormone-independent prostate cancer, B-cell proliferative disorders such as B cell non-Hodgkin's lymphoma, and advanced cancers of kidney, breast, colon, lung, brain, and other tissues.

In yet another aspect, the present invention provides a method of generating an IL-6 antagonist described in various embodiments above. In particular, the present invention provides a method of generating an IL-6 antagonist by (a) first generating antibodies against a complex of IL-6 and IL-6Ralpha by immunizing an animal with a composition including IL-6 and IL-6Ralpha, and (b) identifying an antibody that inhibits the interaction between gp130 and IL-6. The IL-6 and IL-6Ralpha may be in a fusion protein configuration to facilitate formation of the IL-6/IL-6Ralpha complex. In a preferred embodiment, the composition also includes an additional moiety that facilitates antigen presentation, such as an Fc moiety.

In yet another aspect, the present invention provides an antibody specific for a complex of IL-6 and IL-6Ralpha and capable of preventing IL-6 binding to gp130.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTION OF THE DRAWINGS

FIG. 1A depicts undesired activation of gp130 on diseased cells or other target cells resulting from IL-6 overproduction.

FIG. 1B depicts an IL-6 antagonist that sterically blocks the interaction between IL-6 and gp130 and whose binding to IL-6 is not affected by pre-bound sIL-6Ralpha.

FIG. 2 shows an alignment of exemplary antibody V region sequences of the present invention. Positions of variation among the sequences are indicated with arrows. The CDRs are boxed.

FIG. 3 is a schematic depiction of exemplary protein embodiments used in the present invention.

FIGS. 10B-1 and 10B-2 depict experimental results reflecting that the exemplary antibodies of the invention inhibit proliferation of A431 human epithelial carcinoma cells stimulated by the Fc-IL6Ralpha-IL6 fusion protein.

DETAILED DESCRIPTION OF THE INVENTION

Figure 4:
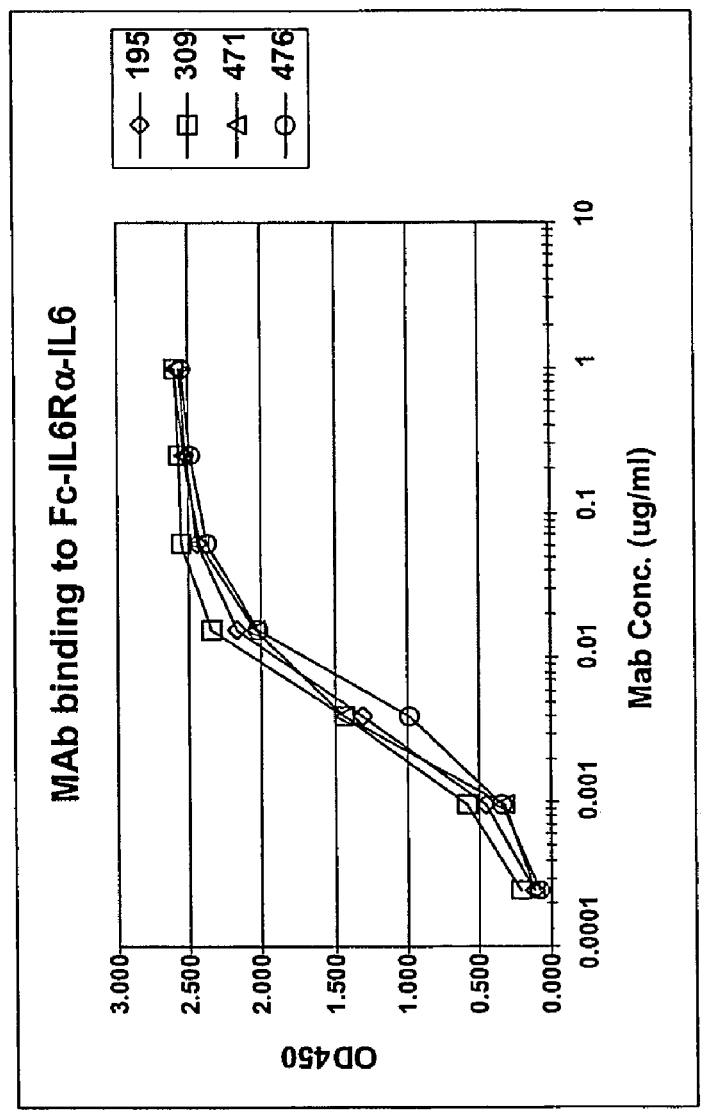
FIG. 4 shows an experimental result reflecting the binding of exemplary antibodies of the invention to Fc-IL6Ralpha-IL6.

The present invention provides a novel IL-6 antagonist that effectively blocks the interaction between IL-6 and gp130, thereby suppressing IL-6 signaling in the presence of preformed IL-6/IL-6Ralpha complexes. As discussed above, since IL-6 is typically complexed with IL-6Ralpha when produced as part of a disease or a disorder, the present invention thus achieves better therapeutic effects compared to existing antibodies that block the interaction between IL-6 and the IL-6Ralpha (van Zaanen et al., (1996) *J. Clin. Invest.*, 98(6):1441-8).

In one particular embodiment, the present invention provides an IL-6 antagonist containing an antibody variable region that binds to a region on IL-6 such that the binding sterically blocks the interaction between IL-6 and gp130. By "sterically block" is meant the means of blocking an interaction between first and second proteins by a third protein's binding to the first protein. The binding between the first and the third proteins prevents the second protein from binding to the first protein due to unfavorable van der Waals or electrostatic interactions between the second and third proteins.

The present invention also provides compositions and methods for treatment of diseases, disorders and side effects involving IL-6 based on the IL-6 antagonist of the invention.

Various aspects of the invention are described in further detail in the following subsections. The use of subsections is not meant to limit the invention. Each subsection may apply to any aspect of the invention. In this application, the use of "or" means "and/or" unless stated otherwise. As used in this disclosure, the term "comprise" and variations of the term, such as "comprising" and "comprises," are not intended to exclude other additives, components, integers or steps.

IL-6 and Its Interaction with IL-6Ralpha and gp130

IL-6 signaling is understood to occur by its interaction with IL-6 receptor alpha (IL-6Ralpha) subunit and gp130, a transmembrane receptor protein that transduces the signals from IL-6 to STAT3, which then activates transcription of various genes. The structure of an extracellular portion of the signaling complex has been determined (Boulanger et al., (2003), *Science*, 300:2101, the teachings of which are hereby incorporated by reference). This structure indicates that the signaling complex contains two copies of IL-6, two copies of the IL-6Ralpha subunit, and two copies of gp130. The structure analysis also indicates that IL-6 binds to the gp130 receptor through three conserved epitopes known as sites I, II, and III. IL-6 must first form a complex with IL-6Ralpha through site I. Site II is a composite epitope formed by the binary complex of IL-6 and IL-6Ralpha, which interacts with cytokine binding region CHR and D2D3 of gp130. Subsequently, site III interacts with the gp130 immunoglobulin-like activation domain (D1 or IGD) to form the competent signaling hexamer complex (Boulanger et al., (2003) *Science*, 300:2101, the teachings of which are hereby incorporated by reference).

The site I binding epitope of IL-6 is localized to the A and D helices and interacts with IL-6Ralpha. The remaining four unique protein-protein interfaces in the hexamer can be separated into two composite sites, sites II and III. Studies of the three dimensional structure of the hexamer complex revealed that a number of residues of IL-6 participate in and important to the interaction between IL-6 and gp130. Such residues include, but are not limited to, Leu19, Arg24, Lys27, Arg30, Tyr31, Asp34 and Trp157.

Thus, the effect of formation of the hexamer complex is to dimerize gp130 and juxtapose its intracellular domains, so that signaling continues at the intracellular level. The IL-6Ralpha subunit does not have an intracellular domain, and serves only to stabilize the complex. Mammalian IL-6 is not capable of binding to gp130 in the absence of IL-6Ralpha. The canonical IL-6Ralpha subunit has three extracellular domains and a transmembrane region that anchors the IL-6Ralpha subunit to the membrane of the expressing cell. "Soluble IL-6Ralpha" or "sIL-6Ralpha" is meant a protein having the extracellular portion of the IL-6Ralpha subunit but lacking the transmembrane segment. The sIL-6Ralpha variant protein, lacking the transmembrane segment, may be generated by translation of an alternatively spliced mRNA encoding IL-6Ralpha, or by proteolytic cleavage of the membrane-bound form of IL-6Ralpha.

sIL-6Ralpha is present in the serum and may also be secreted by the same cell that expresses IL-6. IL-6 forms a complex with sIL-6Ralpha. Once the IL-6/sIL-6Ralpha complex has formed, it is reasonably stable and cannot be bound by an antibody that competes with the IL-6/sIL-6Ralpha interaction. The IL-6/sIL-6Ralpha complex has a significantly extended serum half-life compared to IL-6 alone. Only certain cells in the body, such as B cells, have both IL-6Ralpha and gp130, while many additional cells have only gp130. The IL-6/sIL-6Ralpha complex can bind to cells having only gp130 and stimulate signal transduction. Consequently, undesired activation of gp130 on many cells may result from IL-6 overproduction (FIG. 1A). Therefore, antibodies or other molecules that sterically block the interaction between IL-6 and gp130 may be particularly useful in suppressing undesired IL-6 signaling (see FIG. 1B).

IL-6 Antagonists Sterically Blocking the Interaction with gp130

Thus, as shown in FIG. 1B, the present invention contemplates an IL-6 antagonist that sterically blocks the interaction with gp130 and whose binding to IL-6 is not affected by pre-bound sIL-6Ralpha. "IL-6 antagonists" of the present invention include antibodies or fragments thereof; functional equivalents of antibodies; modified antibodies, such as, single chain antibodies, chimeric antibodies; or other proteins or molecules capable of binding to or associating with IL-6 or IL-6/IL-6Ralpha complex to sterically hinder binding to gp130.

In a preferred embodiment, the IL-6 antagonist of the invention contains an antibody variable region that binds to a region or an epitope on IL-6 or IL-6/IL-6Ralpha complex such that the binding sterically blocks the interaction between IL-6 and gp130. More preferably, the IL-6 antagonist of the invention is an antibody. For example, the binding of the antibody variable region to any regions or epitopes directly participating in the interaction between the IL-6/IL-6Ralpha complex and gp130 is sufficient to sterically interfere with binding to gp130. In addition, the binding to any regions or epitopes adjacent to those directly participating in the interaction may also be sufficient to sterically block the interaction between IL-6/IL-6Ralpha and gp130. Such regions or epitopes may exist on IL-6, IL-6Ralpha, or as composite sites only formed by the complex of IL-6 and IL-6Ralpha. In particular, suitable epitopes to which binding may sterically block the interaction between IL-6 and gp130 include, but are not limited to, any epitopes including at least one of the following amino acids: Leu19, Arg24, Lys27, Arg30, Tyr31, Asp34 and Trp157 of human IL-6.

Generation of Antibodies Sterically Blocking the Interaction Between IL-6 and gp130

Thus, one important feature of the invention is the isolation of antibodies that bind to IL-6/IL-6Ralpha complex and sterically block the IL-6/gp130 interaction. Such antibodies may be polyclonal or monoclonal. According to the invention, such antibodies may be generated by the following method. In a first step, a mouse, rat, rabbit, or other mammal is immunized with a protein composition comprising IL-6 and IL-6Ralpha. It is preferable to have the IL-6 and IL-6Ralpha forming a complex. To facilitate the formation of the complex, IL-6 and IL-6Ralpha may be covalently bound by, for example, chemical cross-linking or by connection through a polypeptide linker. Without wishing to be bound by theory, the goal of such an immunization is that the only exposed surfaces of IL-6 are either surfaces bound by gp130 or are non-neutralizing surfaces. Antibodies that are sterically blocked by IL-6Ralpha should not arise. Particularly preferred immunogens include covalently linked IL-6 and soluble IL-6Ralpha, which may be made by binding IL-6 and IL-6Ralpha in vitro and then treating with a chemical crosslinking agent according to standard procedures, or by expressing IL-6 and soluble IL-6Ralpha as a fusion protein, preferably attached by a linker, for example as described by Peters et al. (*J. Immunol.*, (1998) 161:3575-81, the teaching of which are hereby incorporated by reference). According to the invention, typically, an immunogen fusion protein including IL-6 and IL-6Ralpha also includes an additional moiety that facilitates antigen presentation, such as an Fc region. The protein composition may be administered to a mammal with or without adjuvant according to any of a variety of standard methods. The composition may be administered only once, but is preferably administered more than once according to standard boosting schedules.

As a second step, polyclonal antiserum is harvested from the immunized mammal. The polyclonal serum may be used directly, or may be affinity-purified according to standard methods. Alternatively, the process of generating monoclonal antibodies is initiated. Antibody-producing cells are removed from the immunized animal, for example by surgical removal of the spleen or withdrawal of PBMCs and subsequent sorting. Potential antibody-producing cells are then immortalized by fusion with an immortalized cell line according to standard procedures, cloned into microtiter wells, and screening for production of antibodies that bind to the immunogen.

In another embodiment, as a second step, a display library is generated by isolation of appropriate cells from non-immunized or immunized animals followed by isolation of nucleic acids encoding antibody V regions, insertion of the V region-encoding nucleic acids into phages, yeast, bacteria, or other replicable genetic display systems. The library members are then screened for their capability to bind to IL-6/IL-6Ralpha complexes.

In some embodiment, as a third step, the antibodies produced by monoclonal cell lines or the antibody V regions selected from the library are optionally subjected to secondary screens as follows. Specifically, the antibody clones or the antibody V regions are tested for the ability to bind to IL-6 alone, to bind to IL-6Ralpha alone, to bind to IL-6/IL-6Ralpha complex, and for the ability to inhibit the interaction between an IL-6/IL-6Ralpha complex and gp130. From the results of these tests, the antibodies or antibody V regions can be classified into several groups: neutralizing antibodies that bind to IL-6 and block the interaction with gp130, antibodies that bind to IL-6Ralpha, non-neutralizing antibodies that bind to IL-6, neutralizing antibodies that bind to IL-6/IL-6Ralpha complex but not to IL-6 or IL-6Ralpha alone and block the interaction with gp130, and neutralizing antibodies that bind to IL-6 and block the interaction with IL-6Ralpha. Antibodies of each class except the last are expected. Such binding and signaling assays are well known in the art of protein biochemistry and signal transduction, and specific embodiments are further detailed in the Examples.

Identification of Antibodies not Significantly Extending Serum Half-Life of IL-6

One undesired effect of anti-IL-6 antibodies is that they often prolong the serum half-life of IL-6. The molecular weight of IL-6 is about 25,000 Daltons, which is well below the renal clearance threshold of 50,000 Daltons, while the molecular weight of an antibody-IL-6 complex is over 150,000 Daltons. The formation of anti-IL-6 antibody/antigen complexes generally has the effect of lengthening the serum half-life of IL-6 because the molecular weight of the complex is greater than the renal clearance threshold. Thus, the present invention also provides methods to identify antibodies that bind to IL-6 or IL-6/IL-6Ralpha complex but do not significantly extend the serum half-life of IL-6.

The method involves, as a first step, the isolation of a panel of anti-IL-6 antibodies. As a second step, the antibodies are then tested for their effect on IL-6 serum half-life, for example as follows. IL-6 is administered to an animal such as a rodent. It is convenient to use a labeled form of IL-6, such as radioactive IL-6. An antibody to be tested is also administered to the same animal, preferably by a different route of administration. As a negative control, PBS is administered in place of either the antibody or the IL-6. Serum samples are obtained at various times after administration of the proteins, and tested for levels of IL-6 and the antibody according to standard techniques. For example, radiolabelled, iodinated IL-6 may be quantitated using a radiation counter, and the antibody may be detected by an ELISA method based on IL-6 capture.

It is contemplated that some antibodies have an extended pharmacokinetic profile compared to others, and some antibodies cause an enhancement of the pharmacokinetics of IL-6 while other antibodies cause only a moderate extension or essentially none at all. Depending on the particular application, one class of preferred antibodies of the invention are those that themselves have a favorable pharmacokinetic profile, but do not significantly extend the pharmacokinetic profile of IL-6.

Sequences of Antibody Variable Regions

The sequences of antibody V regions identified according to the methods described above are characterized using standard sequencing methods known in the art. An exemplary method is described in detail in Example 4. Exemplary sequences of antibody heavy chain and light chain V regions that bind to IL-6 and block its interaction with gp130 are shown in FIG. 2. FIG. 2 also illustrates an alignment of the antibody V region sequences identified according to the present invention. Position variation among the sequences are indicated with arrows. The CDR regions are boxed.

The V regions of the invention may be configured with human constant regions to form a chimeric antibody. An exemplary chimeric antibody may include VH and VL regions described in FIG. 2 and constant regions derived from IgG1, IgG2, IgG3, IgG4, IgA, IgD, or IgM. Alternatively, the antibodies of the invention may be expressed with hybrid isotype constant regions, as described in PCT publication WO 02/072605, the disclosures of which are hereby incorporated by reference. The V regions of the invention may also be configured as Fab moieties, "minibodies" lacking the CH2 domain, or as single-chain Fv moieties. These latter configurations are smaller than whole antibodies and have enhanced diffusion characteristics, which may be useful in situations requiring efficient tissue penetration, such as in treatment of tumors that secrete IL-6.

Expression

The antibodies and proteins containing antibody variable regions of the invention are preferably expressed in mammalian cells, such as NS/0 cells, CHO cells, SP2/0 cells, BHK cells, or other mammalian cells. The expression of antibodies in mammalian cells is well known in the art of protein engineering. The antibodies may also be expressed in plant cells such as corn or tobacco, insect cells such as via a baculovirus vector, fungal cells such as S. cerevisiae or Pichia pastoris, or in bacterial cells, which are most useful in expressing smaller configurations such as single-chain Fv molecules.

Administration

The IL-6 antagonists of the invention are used in the treatment of a variety of diseases and disorders involving expression of IL-6. Such diseases and disorders include, but are not limited to, cancers such as hormone-independent prostate cancer, B-cell proliferative disorders such as B cell non-Hodgkin's lymphoma, and advanced cancers of kidney, breast, colon, lung, brain, and other tissues; antibody-driven autoimmune disorders such as rheumatoid arthritis, myasthenia gravis, systemic lupus erythematosis, and other autoimmune diseases; or osteoporosis. The molecules of the invention may also be used to treat cachexia in cancer patients, which often results from overproduction of IL-6 and IL-6Ralpha by tumors.

The antagonists of the invention may cause a target-related side effect of immunosuppression, particularly inhibition of antibody formation. When a patient is receiving an antibody of the invention, it is often useful to supplement the treatment with a prophylatic anti-infective agent. Such prophylactic treatments are well known in the art of treating immunosuppressed patients.

An antagonist of the invention is typically administered by infusion, but may also be administered by subcutaneous, intradermal, intramuscular, or intraperitoneal injection, inhalation, or oral administration. For a 70 kilogram adult human, a dose in the range of about 50 to 2000 milligrams is preferred, with a dose in the range of 100-800 milligrams more preferred, and a dose of about 300-600 milligrams is most preferred.

The precise dose may be adjusted on a patient-by-patient basis. For example, when treating a solid tumor in a patient, the effectiveness of a given dose may be evaluated as follows. At various points after administration of an antibody of the invention, biopsies of the tumor are withdrawn and tested for gp130 activation, for example by immunostaining with an appropriate anti-phosphotyrosine antibody. The goal is to have continuous, essentially complete inhibition of gp130 activation in the tumor. If inhibition of gp130 activation is not complete, the dose may be increased or the dosage frequency may be increased.

It should be understood that the above-described embodiments and the following examples are given by way of illustration, not limitation. Various changes and modifications within the scope of the present invention will become apparent to those skilled in the art from the present description.

EXAMPLES

Example 1

Expression of an IL-6/IL-6Ralpha Complex for Use as an Antigen

To generate antibodies that bind to a surface of IL-6 that interferes with its binding to gp130 and is accessible in an IL-6/IL-6Ralpha complex, a fusion protein comprising an Fc domain, the extracellular domains of IL-6Ralpha, and IL-6 was expressed from a plasmid termed pdCs-Fc-IL6Ralpha-IL6. The fusion protein is referred to herein as Fc-IL6Ralpha-IL6. The Fc domain was derived from mouse $IgG_{\gamma 2a}$, and the IL-6Ralpha and IL-6 were based on the human sequences. The sequence of this protein and the DNA encoding this protein are shown below.

```
Protein sequence of Fc-IL6Ralpha-IL6
(SEQ ID NO:37):
EPRGPTIKPCPPCKCPAPNLLGGPSVFIFPPKIKDVLMISLSPIVTCVVV

DVSEDDPDVQISWFVNNVEVHTAQTQTHREDYNSTLRVVSALPIQHQDWM

SGKEFKCKVNNKDLPAPIERTISKPKGSVRAPQVYVLPPPEEEMTKKQVT

LTCMVTDFMPEDIYVEWTNNGKTELNYKNTEPVLDSDGSYFMYSKLRVEK

KNWVERNSYSCSVVHEGLHNHHTFKSFSRTPGSGDDDDDKLPPEEPQLSC

FRKSPLSNVVCEWGPRSTPSLTTKAVLLVRKFQNSPAEDFQEPCQYSQES

QKFSCQLAVPEGDSSFYIVSMCVASSVGSKFSKTQTFQGCGILQPDPPAN

ITVTAVARNPRWLSVTWQDPHSWNSSFYRLRFELRYRAERSKTFTTWMVK

DLQHHCVIHDAWSGLRHVVQLRAQEEFGQGEWSEWSPEAMGTPWTESRSP

PARGGGGSGGGGSVEPVPPGEDSKDVAAPHRQPLTSSERIDKQIRYILDG

ISALRKETCNKSNMCESSKEALAENNLNLPKMAEKDGCFQSGFNEETCLV

KIITGLLEFEVYLEYLQNRFESSEEQARAVQMSTKVLIQFLQKKAKNLDA

ITTPDPTTNASLLTKLQAQNQWLQDMTTHLILRSFKEFLQSSLRALRQM

DNA sequence encoding mature Fc-IL6Ralpha-IL6
(SEQ ID NO:38):
GAGCCCAGAGGGCCCACAATCAAGCCCTGTCCTCCATGCAAATGCCCAGC

ACCTAACCTCTTGGGTGGACCATCCGTCTTCATCTTCCCTCCAAAGATCA

AGGATGTACTCATGATCTCCCTGAGCCCCATAGTCACATGTGTGGTGGTG

GATGTGAGCGAGGATGACCCAGATGTCCAGATCAGCTGGTTTGTGAACAA

CGTGGAAGTACACACAGCTCAGACACAAACCCATAGAGAGGATTACAACA

GTACTCTCCGGGTGGTCAGTGCCCTCCCCATCCAGCACCAGGACTGGATG

AGTGGCAAGGAGTTCAAATGCAAGGTCAACAACAAAGACCTCCCAGCGCC

CATCGAGAGAACCATCTCAAAACCCAAAGGGTCAGTAAGAGCTCCACAGG

TATATGTCTTGCCTCCACCAGAAGAAGAGATGACTAAGAAACAGGTCACT

CTGACCTGCATGGTCACAGACTTCATGCCTGAAGACATTTACGTGGAGTG

GACCAACAACGGGAAAACAGAGCTAAACTACAAGAACACTGAACCAGTCC

TGGACTCTGATGGTTCTTACTTCATGTACAGCAAGCTGAGAGTGGAAAAG

AAGAACTGGGTGGAAAGAAATAGCTACTCCTGTTCAGTGGTCCACGAGGG
```

-continued

```
TCTGCACAATCACCACACGACTAAGAGCTTCTCCCGGAGCCCGGGTTCAG

GGGATGACGATGACGATAAGCTTCCCCCCGAGGAGCCCCAGCTCTCCTGC

TTCCGGAAGAGCCCCCTCAGCAATGTTGTTTGTGAGTGGGGTCCTCGGAG

CACCCCATCCCTGACGACAAAGGCTGTGCTCTTGGTGAGGAAGTTTCAGA

ACAGTCCGGCCGAAGACTTCCAGGAGCCGTGCCAGTATTCCCAGGAGTCC

CAGAAGTTCTCCTGCCAGTTAGCAGTCCCGGAGGGAGACAGCTCTTTCTA

CATAGTGTCCATGTGCGTCGCCAGTAGTGTCGGGAGCAAGTTCAGCAAAA

CTCAAACCTTTCAGGGTTGTGGAATCTTGCAGCCTGATCCGCCTGCCAAC

ATCACAGTCACTGCCGTGGCCAGAAACCCCGCTGGCTCAGTGTCACCTG

GCAAGACCCCCACTCGTGGAACTCATCTTTCTACAGACTACGGTTTGAGC

TCAGATATCGGGCTGAACGGTCAAAGACATTCACAACATGGATGGTCAAG

GACCTCCAGCATCACTGTGTCATCCACGACGCCTGGAGCGGCCTGAGGCA

CGTGGTGCAGCTTCGTGCCCAGGAGGAGTTCGGGCAAGGCGAGTGGAGCG

AGTGGAGCCCGGAGGCCATGGGCACGCCTTGGACAGAATCCAGGAGTCCT

CCAGCTAGAGGGGCGGGGCAGTGGGGCGGGGCAGTGTAGAACCGGT

ACCCCCAGGAGAAGATTCCAAAGATGTAGCTGCCCCACACAGACAGCCAC

TCACCTCTTCAGAACGAATTGACAAACAAATTCGGTACATCCTCGACGGC

ATCTCAGCCCTGAGAAAGGAGACATGTAACAAGAGTAACATGTGTGAAAG

CAGCAAAGAGGCACTGGCAGAAAACAACCTGAACCTTCCAAAGATGGCTG

AAAAAGATGGATGCTTCCAATCTGGATTCAATGAGGAGACTTGCCTGGTG

AAAATCATCACTGGTCTTTTGGAGTTTGAGGTATACCTAGAGTACCTCCA

GAACAGATTTGAGAGTAGTGAGGAACAAGCCAGAGCTGTGCAGATGAGTA

CAAAAGTCCTGATCCAGTTCCTGCAGAAAAAGGCAAAGAATCTAGATGCA

ATAACCACCCCTGACCCAACCACAAATGCCAGCCTGCTGACGAAGCTGCA

GGCACAGAACCAGTGGCTGCAGGACATGACAACTCATCTCATTCTGCGCA

GCTTTAAGGAGTTCCTGCAGTCCAGCCTGAGGGCTCTTCGGCAAATGTAG
```

For rapid analysis of protein expression to characterize the Fc-IL6Ralpha-IL6 fusion protein product, the plasmid pdCs-Fc-IL6Ralpha-IL6 was introduced into human embryonic kidney HEK 293 cells (ATCC# CRL-1573) by transient transfection using lipofectamine (Invitrogen).

To obtain stably transfected clones which express Fc-IL6Ralpha-IL6, the appropriate plasmid DNA was introduced into the mouse myeloma NS/0 cells by electroporation. NS/0 cells were grown in Dulbecco's modified Eagle's medium supplemented with 10% heat-inactivated fetal bovine serum, 2 mM glutamine and penicillin/streptomycin. About 5×106 cells were washed once with PBS and resuspended in 0.5 ml PBS. 10 μg of linearized plasmid DNA were then incubated with the cells in a Gene Pulser® Cuvette (0.4 cm electrode gap, BioRad) on ice for 10 min. Electroporation was performed using a Gene Pulser® (BioRad, Hercules, Calif.) with settings at 0.25 V and 500 μF. Cells were allowed to recover for 10 min on ice, after which they were resuspended in growth medium and plated onto two 96 well plates. Stably transfected clones were selected by their growth in the presence of 100 nM methotrexate (MTX), which was added to the growth medium two days post-transfection. The cells were fed every 3 days for two to three more times, and MTX-resistant clones appeared in 2 to 3 weeks. Supernatants from clones were assayed by anti-Fc ELISA to identify high producers. High producing clones were isolated and propagated in growth medium containing 100 nM MTX. The growth medium typically used was H-SFM or CD medium (Life Technologies).

The Fc-IL6Ralpha-IL6 fusion protein was subsequently captured from the medium for further analysis. For routine characterization by gel electrophoresis, the Fc-IL6Ralpha-IL6 fusion proteins secreted into the medium was captured on Protein A Sepharose® beads (Repligen, Cambridge, Mass.) and then eluted by boiling the sample in protein sample buffer, with or without a reducing agent such as β-mercaptoethanol. The samples were analyzed by SDS-PAGE and the protein bands were visualized by Coomassie staining.

It will be recognized by those skilled in the art that any of a variety of proteins could be used as alternatives to the Fc-IL6Ralpha-IL6 protein described above. For example, other configurations of IL-6Ralpha and IL-6 could be used, such as IL-6Ralpha-IL-6-Fc, albumin-IL-6Ralpha-IL-6, cytokine-IL-6Ralpha-IL-6, where the cytokine is chosen to stimulate an immune response against the IL-6/IL-6Ralpha complex. Proteins comprising a cytokine, an Fc moiety, and an IL-6Ralpha/IL-6 complex may also be used, for example, according to the methods of Gillies et al. (WO01/07081, the disclosures of which are hereby incorporated by reference). Finally, IL-6 and IL-6Ralpha may be produced separately, chemically cross-linked, and used as an antigen. When an Fc moiety and/or a secondary cytokine moiety are used, it is generally advantageous that these moieties be from the animal that is being immunized, such as a mouse.

In preparation for the characterization of the antibodies described below, DNAs encoding Fc-IL6 and Fc-IL6Ralpha were constructed similarly as described above. The corresponding proteins were purified similarly as described above. In addition, human IL-6, human IL-6Ralpha, and human gp130-Fc were purchased from R&D Systems, Inc. for use in certain experiments below. Schematic depictions of these proteins used in the experiments are shown in FIG. 3. The protein and DNA sequences of relevant constructs are provided as follows.

```
Mature Fc-IL6Ralpha
                                          (SEQ ID NO:39)
EPRGPTIKPCPPCKCPAPNLLGGPSVFIFPPKIKDVLMISLSPIVTCVVV

DVSEDDPDVQISWFVNNVEVHTAQTQTHREDYNSTLRVVSALPIQHQDWM

SGKEFKCKVNNKDLPAPIERTISKPKGSVRAPQVYVLPPPEEEMTKKQVT

LTCMVTDFMPEDIYVEWTNNGKTELNYKNTEPVLDSDGSYFMYSKLRVEK

KNWVERNSYSCSVVHEGLHNHHTTKSFSRTPGSGDDDDDKLPPEEPQLSC

FRKSPLSNVVCEWGPRSTPSLTTKAVLLVRKFQNSPAEDFQEPCQYSQES

QKFSCQLAVPEGDSSFYIVSMCVASSVGSKFSKTQTFQGCGILQPDPPAN

ITVTAVARNPRWLSVTWQDPHSWNSSFYRLRFELRYRAERSKTFTFFWMV

KDLQHHCVIHDAWSGLRHVVQLRAQEEFGQGEWSEWSPEAMGTPWTESRS

PPA

DNA encoding mature Fc-IL6Ralpha
                                          (SEQ ID NO:40)
GAGCCCAGAGGGCCCACAATCAAGCCCTGTCCTCCATGCAAATGCCCAGC

ACCTAACCTCTTGGGTGGACCATCCGTCTTCATCTTCCCTCCAAAGATCA
```

```
AGGATGTACTCATGATCTCCCTGAGCCCCATAGTCACATGTGTGGTGGTG

GATGTGAGCGAGGATGACCCAGATGTCCAGATCAGCTGGTTTGTGAACAA

CGTGGAAGTACACACAGCTCAGACACAAACCCATAGAGAGGATTACAAC

GTACTCTCCGGGTGGTCAGTGCCCTCCCCATCCAGCACCAGGACTGGATG

AGTGGCAAGGAGTTCAAATGCAAGGTCAACAACAAAGACCTCCCAGCGCC

CATCGAGAGAACCATCTCAAAACCCAAAGGGTCAGTAAGAGCTCCACAGG

TATATGTCTTGCCTCCACCAGAAGAAGAGATGACTAAGAAACAGGTCACT

CTGACCTGCATGGTCACAGACTTCATGCCTGAAGACATTTACGTGGAGTG

GACCAACAACGGGAAAACAGAGCTAAACTACAAGAACACTGAACCAGTCC

TGGACTCTGATGGTTCTTACTTCATGTACAGCAAGCTGAGAGTGGAAAAG

AAGAACTGGGTGGAAAGAAATAGCTACTCCTGTTCAGTGGTCCACGAGGG

TCTGCACAATCACCACACGACTAAGAGCTTCTCCCGGACCCCGGGTTCAG

GGGATGACGATGACGATAAGCTTCCCCCCGAGGAGCCCCAGCTCTCCTGC

TTCCGGAAGAGCCCCCTCAGCAATGTTGTTTGTGAGTGGGGTCCTCGGAG

CACCCCATCCCTGACGACAAAGGCTGTGCTCTTGGTGAGGAAGTTTCAGA

ACAGTCCGGCCGAAGACTTCCAGGAGCCGTGCCAGTATTCCCAGGAGTCC

CAGAAGTTCTCCTGCCAGTTAGCAGTCCCGGAGGGAGACAGCTCTTTCTA

CATAGTGTCCATGTGCGTCGCCAGTAGTGTCGGGAGCAAGTTCAGCAAAA

CTCAAACCTTTCAGGGTTGTGGAATCTTGCAGCCTGATCCGCCTGCCAAC

ATCACAGTCACTGCCGTGGCCAGAAACCCCGCTGGCTCAGTGTCACCTG

GCAAGACCCCCACTCCTGGAACTCATCTTTCTACAGACTACGGTTTGAGC

TCAGATATCGGGCTGAACGGTCAAAGACATTCACAACATGGATGGTCAAG

GACCTCCAGCATCACTGTGTCATCCACGACGCCTGGAGCGGCCTGAGGCA

CGTGGTGCAGCTTCGTGCCCAGGAGGAGTTCGGGCAAGGCGAGTGGAGCG

AGTGGAGCCCGGAGGCCATGGGCACGCCTTGGACAGAATCCAGGAGTCCT

CCAGCTTAG
```

Mature Fc-IL6
(SEQ ID NO:41)
EPRGPTIKPCPPCKCPAPNLLGGPSVFIFPPKIKDVLMISLSPIVTCVVV

DVSEDDPDVQISWFVNNVEVHTAQTQTHREDYNSTLRVVSALPIQHQDWM

SGKEFKCKVNNKDLPAPIERTISKPKGSVRAPQVYVLPPPEEEMTKKQVT

LTCMVTDFMPEDIYVEWTNNGKTELNYKNTEPVLDSDGSYFMYSKLRVEK

KNWVERNSYSCSVVHEGLHNHHTTKSFSRTPGKEDSKDVAAPHRQPLTSS

ERIDKQIRYILDGISALRKETCNKSNMCESSKEALAENNLNLPKMAEKDG

CFQSGFNEETCLVKIITGLLEFEVYLEYLQNRFESSEEQARAVQMSTKVL

IQFLQKKAKNLDAITTPDPTTNASLLTKLQAQNQWLQDMFTTHLILRSFK

EFLQSSLRALRQM

DNA encoding mature Fc-IL6
(SEQ ID NO:42)
```
GAGCCCAGAGGGCCCACAATCAAGCCCTGTCCTCCATGCAAATGCCCAGC

ACCTAACCTCTTGGGTGGACCATCCGTCTTCATCTTCCCTCCAAAGATCA

AGGATGTACTCATGATCTCCCTGAGCCCCATAGTCACATGTGTGGTGGTG

GATGTGAGCGAGGATGACCCAGATGTCCAGATCAGCTGGTTTGTGAACA

ACGTGGAAGTACACACAGCTCAGACACAAACCCATAGAGAGGATTACAAC

AGTACTCTCCGGGTGGTCAGTGCCCTCCCCATCCAGCACCAGGACTGGAT

GAGTGGCAAGGAGTTCAAATGCAAGGTCAACAACAAAGACCTCCCAGCGC

CCATCGAGAGAACCATCTCAAAACCCAAAGGGTCAGTAAGAGCTCCACAG

GTATATGTCTTGCCTCCACCAGAAGAAGAGATGACTAAGAAACAGGTCAC

TCTGACCTGCATGGTCACAGACTTCATGCCTGAAGACATTTACGTGGAGT

GGACCAACAACGGGAAAACAGAGCTAAACTACAAGAACACTGAACCAGTC

CTGGACTCTGATGGTTCTTACTTCATGTACAGCAAGCTGAGAGTGGAAAA

GAAGAACTGGGTGGAAAGAAATAGCTACTCCTGTTCAGTGGTCCACGAGG

GTCTGCACAATCACCACACGACTAAGAGCTTCTCCCGGACCCCGGGTAAA

GAAGATTCCAAAGATGTAGCTGCCCCACACAGACAGCCACTCACCTCTTC

AGAACGAATTGACAAACAAATTCGGTACATCCTCGACGGCATCTCAGCCC

TGAGAAAGGAGACATGTAACAAGAGTAACATGTGTGAAAGCAGCAAAGAG

GCACTGGCAGAAAACAACCTGAACCTTCCAAAGATGGCTGAAAAGATGG

ATGCTTCCAATCTGGATTCAATGAGGAGACTTGCCTGGTGAAAATCATCA

CTGGTCTTTTGGAGTTTGAGGTATACCTAGAGTACCTCCAGAACAGATTT

GAGAGTAGTGAGGAACAAGCCAGAGCTGTGCAGATGAGTACAAAAGTCCT

GATCCAGTTCCTGCAGAAAAAGGCAAAGAATCTAGATGCAATAACCACCC

CTGACCCAACCACAAATGCCAGCCTGCTGACGAAGCTGCAGGCACAGAAC

CAGTGGCTGCAGGACATGACAACTCATCTCATTCTGCGCAGCTTTAAGGA

GTTCCTGCAGTCCAGCCTGAGGGCTCTTCGGCAAATGTAG
```

Example 2

Immunization with an IL-6/IL-6Ralpha Complex

Twenty mice (Balb/C) were immunized with the Fc-IL6Ralpha-IL6 protein produced as described in Example 1, and monoclonal antibodies to this protein were produced according to a modification of the method of Kohler and Milstein (1975) (*Nature,* 256:495-7). Specifically, 1 microgram of Fc-IL6Ralpha-IL6 was injected subcutaneously with 100 microliters of complete Freund's adjuvant. Injections were repeated 14 days later, using 1 microgram of protein injected intraperitoneally with 100 microliters of incomplete Freund's adjuvant. 24 days after the first injection, mice were boosted with 1 microgram of Fc-IL6Ralpha-IL6 protein in 100 microliters of PBS intravenously. Three days later mice were sacrificed and spleens excised, and spleen cells cultured according to standard procedures. 435 million spleen cells from two mice with strong polyclonal anti-IL6Ralpha/IL6 responses were fused with 175 million NS/0 cells at a ratio of 2.4 spleen cells to 1 NS/0 cell. Immortalized B cell/NS/0 cell hybrids were produced according to standard procedures, and hybridomas were then screened for the production of antibodies against the Fc-IL6Ralpha-IL6 fusion protein using ELISA Technology.

Example 3

Screening for Antibodies that Block the Interaction Between the IL-6/IL-6Ralpha Complex and gp130

Binding

Positive clones from Example 2 were further tested as follows. The isotype of the antibody was determined, and IgM-based clones were not characterized further. IgG-based monoclonal antibodies were tested for their ability to bind to either IL-6 or IL-6Ralpha using immobilized Fc-IL6 and Fc-IL6Ralpha according to standard procedures. Some clones bound to IL-6, some bound to IL-6Ralpha, and some bound to neither proteins, suggesting that these monoclonals might recognize some portion of the linker or might recognize composite epitopes consisting both IL-6 and IL-6Ralpha moieties.

Figure 5:
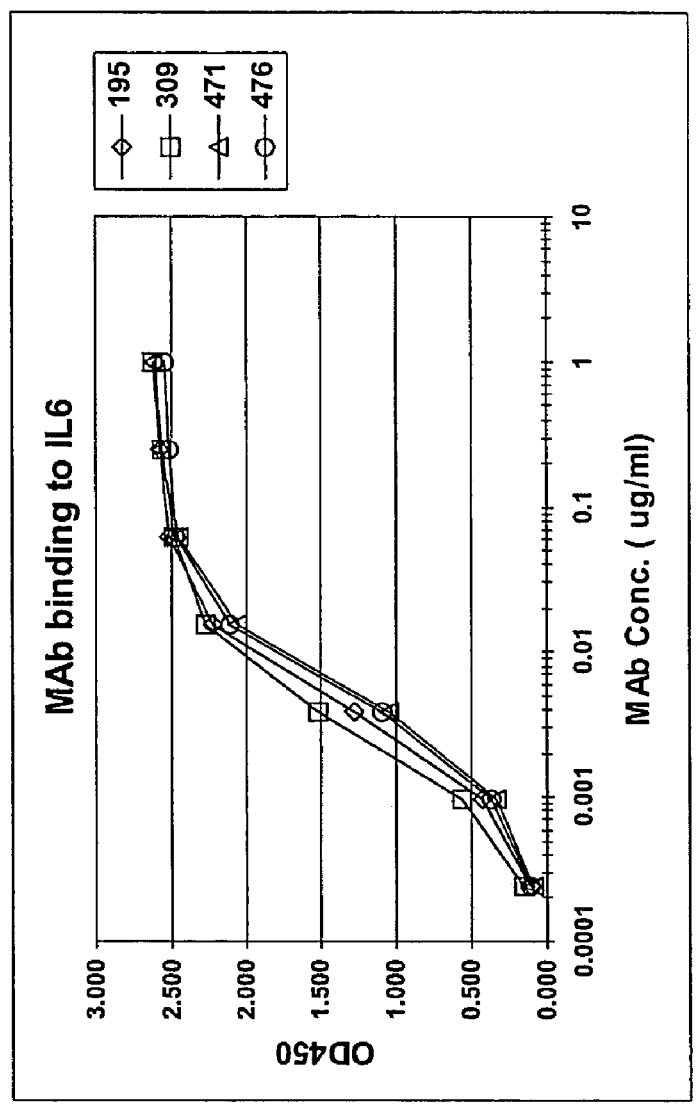
FIG. 5 shows an experimental result reflecting the binding of exemplary antibodies of the invention to IL-6.
Figure 6:
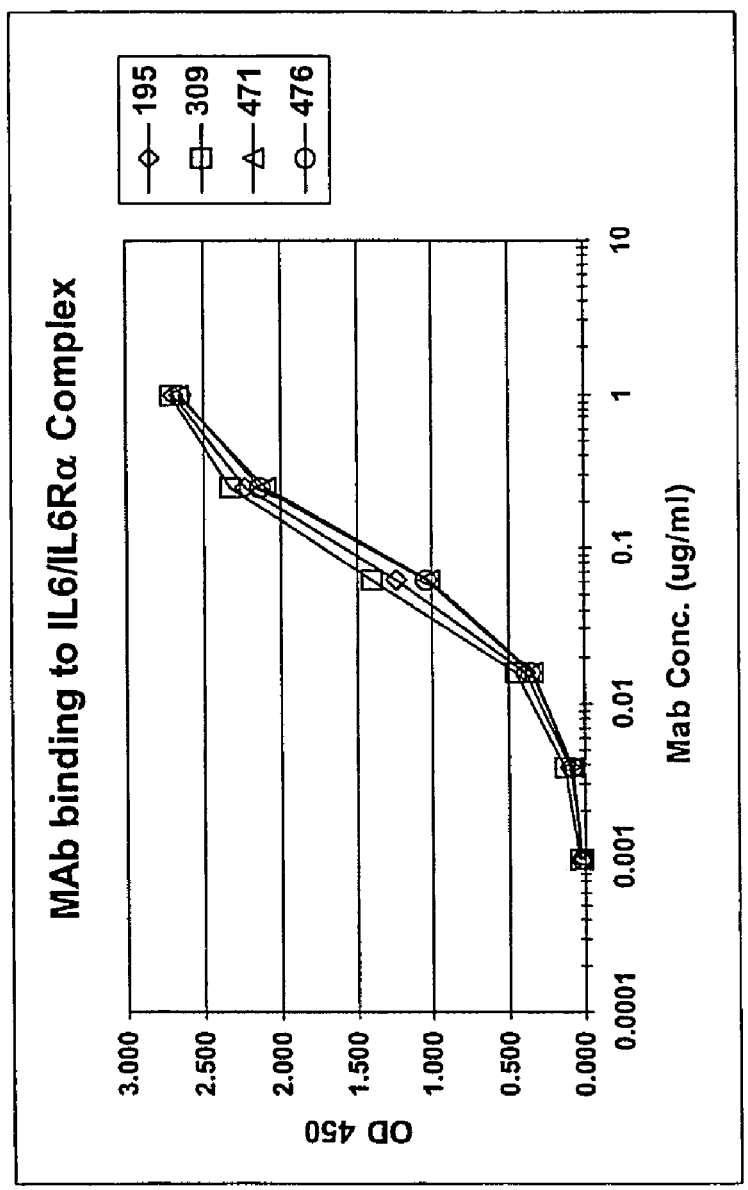
FIG. 6 shows an experimental result reflecting the binding of exemplary antibodies of the invention to non-covalently complexed IL-6 and IL-6Ralpha.
Figure 7:
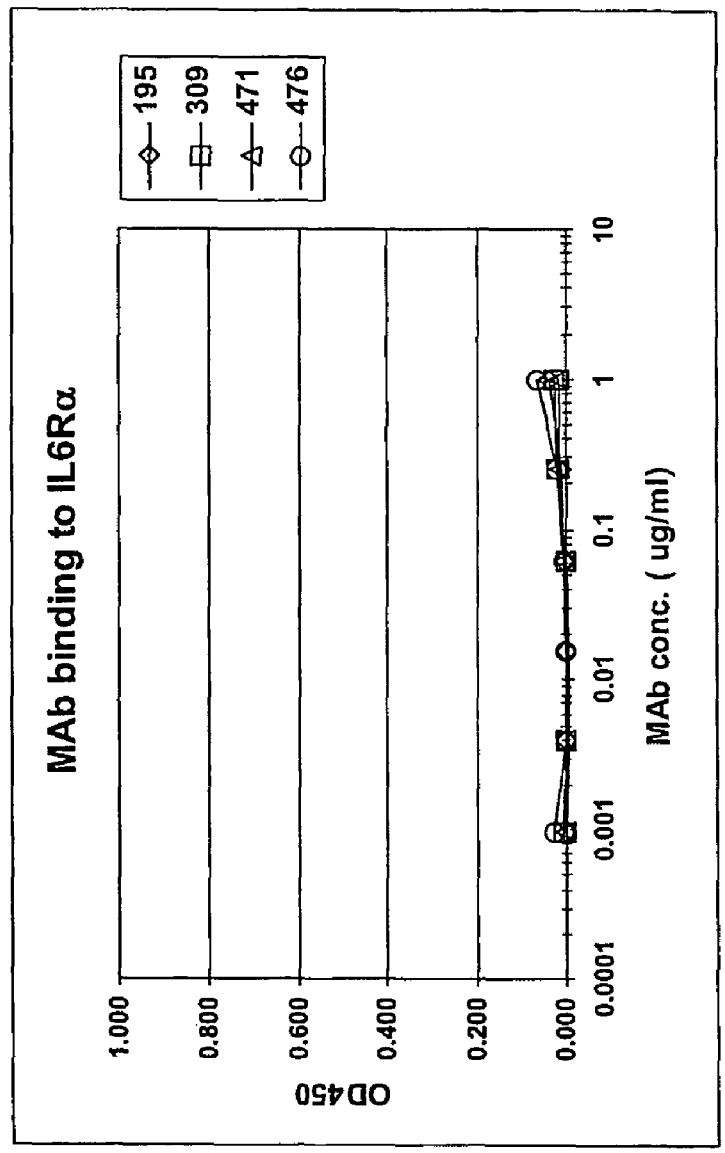
FIG. 7 shows an experimental result reflecting the binding of exemplary antibodies of the invention to IL-6Ralpha alone.

Exemplary results of the binding characteristics of typical antibodies of the invention are shown in FIG. 4 (binding to Fc-IL6Ralpha-IL6), FIG. 5 (binding to IL-6), FIG. 6 (binding to non-covalently complexed IL-6 and IL-6Ralpha), and FIG. 7 (IL-6Ralpha alone). The results indicate that, for this set of antibodies, binding to IL-6 and covalently linked IL-6 and IL-6Ralpha was similar, binding to a non-covalent IL-6/IL-6Ralpha complex gave a less strong signal (possibly because of dissociation of IL-6 from IL-6R during washing steps), and binding to IL-6Ralpha alone could not be detected.

Competition Tests

To further characterize the antibodies that recognize IL-6, the following competition tests were performed. First, the ability of the monoclonal antibodies to inhibit the interaction between Fc-IL6Ralpha-IL6 and gp130-Fc was tested. The inhibition assays were performed based on the methods described by Scheller et al. *J. Immuno. Methods,* 291:93-100 (2004), the teachings of which are hereby incorporated by reference. Four antibodies, named Mab#195, Mab#309, Mab#471, and Mab#476 were identified that blocked this interaction. Second, inhibition of the interaction between Fc-IL6 and Fc-IL6Ralpha by the antibodies was tested. None of the antibodies were found to inhibit this interaction, which was expected based on the fact that the antibodies derived from an immunization with Fc-IL6Ralpha-IL6 and underwent an initial screen for binding to Fc-IL6Ralpha-IL6.

Figure 8:
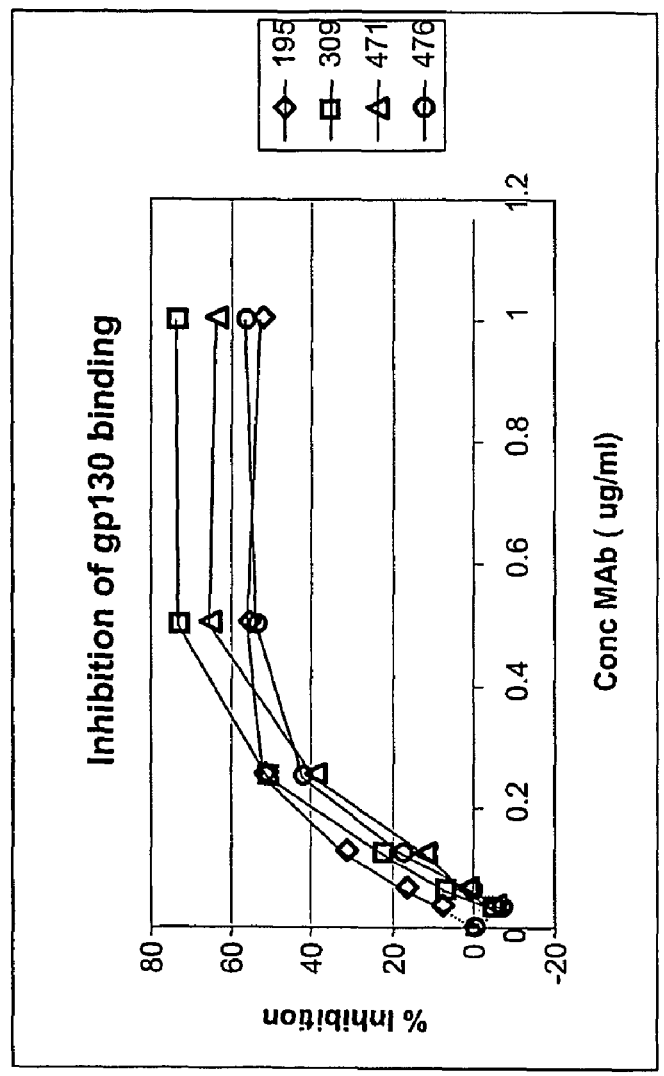
FIG. 8 shows an experimental result illustrating that the exemplary antibodies of the invention inhibit the interaction between Fc-IL6Ralpha-IL6 and gp130.

Typical results illustrating the inhibition of the interaction between Fc-IL6Ralpha-IL6 and gp130-Fc are shown in FIG. 8.

Cell-Based Assay

Antibodies Mab#195, Mab#309, Mab#471, and Mab#476 were tested for their ability to block haptoglobin release from HepG2 cells stimulated with an Fc-IL6Ralpha-IL6 complex. Haptoglobin is a protein secreted by liver cells during inflammatory states. HepG2 cells are a liver cell line. The release of haptoglobin from HepG2 cells provides a convenient bioassay for the activity of IL-6Ralpha/IL-6 complexes.

Figure 9:
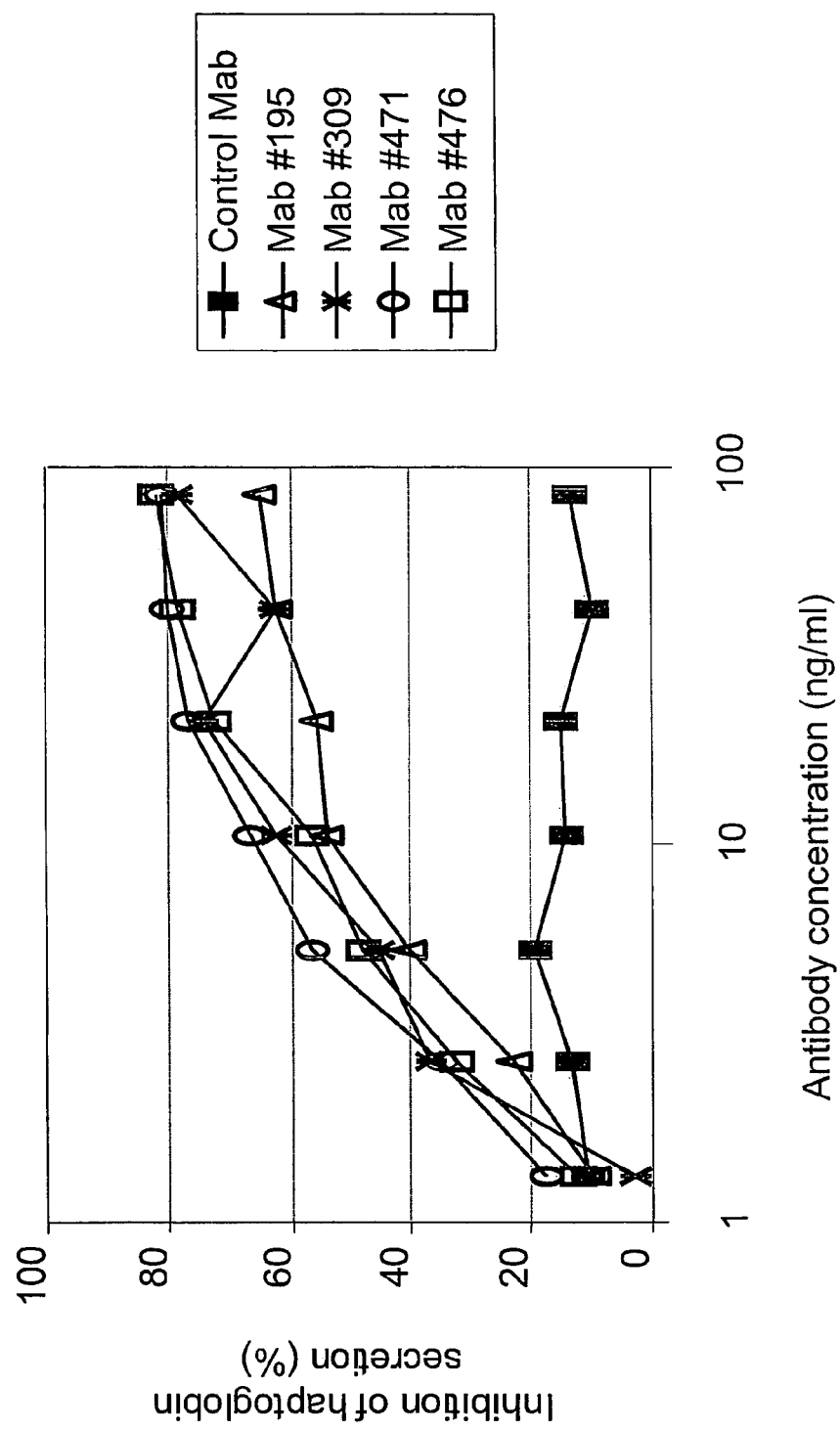
FIG. 9 shows an experimental result illustrating the ability to block haptoglobin release from HepG2 cells stimulated with an Fc-IL6Ralpha-IL6 complex by exemplary antibodies of the invention.

The assay was performed as follows. HepG2 cells were plated at 0.1×106 cells per well in a 96-well plate, and allowed to grow in DMEM supplemented with 10% Fetal Bovine Serum (FBS) medium overnight. Cells were then washed with PBS, and incubated in starving medium, DMEM without FBS, for 1 hour at 37 oC. The cells were then incubated in stimulating medium, DMEM (without FBS) in the presence of 8 ng/ml Fc-IL6Ralpha-IL6 complex, and various concentrations of test antibody supplemented for 22 hours. Supernatants were withdrawn and the levels of haptoglobin were determined by an ELISA for haptoglobin detection. A standard ELISA procedure was followed, using a goat anti-human haptoglobin antibody (Sigma #H5015) for capture, a mouse anti-human haptoglobin antibody (US Biological #H1820-05) as a primary and an anti-mouse IgG-HRP antibody (Promega #W402B) as a secondary antibody. Typical results are shown in FIG. 9.

Biacore Analysis

The binding of antibodies Mab#195, Mab#309, Mab#471, and Mab#476 to IL-6 was quantitatively characterized using a Biacore machine. The antibodies were immobilized on a chip; IL-6 protein was passed over the chip, and on-rates and off-rates were measured. The following results were obtained.

| Parameter | mAb#195 | mAb#309 | mAb#471 | mAb#476 |
|---|---|---|---|---|
| $k_a$ (1/Ms) | $2.4 \times 10^6$ | $8 \times 10^5$ | $1.8 \times 10^6$ | $2.5–2.6 \times 10^6$ |
| $k_d$ (1/s) | $4.8 \times 10^{-3}$ | $1.1 \times 10^{-4}$ | $1.4 \times 10^{-5}$ | $1.2–2.6 \times 10^{-4}$ |
| $K_D$ (pM) | 2000 | 135 | 7.5 | 47–106 |

Inhibition of Proliferation of Cancer Cell Lines

The antibodies of the invention were tested for their ability to inhibit the proliferation of A431 cells and LP-1 cells. Inhibition of the proliferation of LP-1 cells is described in Example 8. Inhibition of proliferation of A431 was measured as follows. On day 1, cells were plated in 96-well plates at 25,000 cells/well in DMEM containing 10% FBS, with 200 microliters per well. On day 3, cells were washed once with 200 microliters of PBS. Cells were starved for one hour at 37° C. in 100 microliters of DMEM.

On day 3, dilutions of anti-IL-6 antibodies were prepared in 96 U-bottom plates in DMEM containing IL6Ralpha-IL6-His6 (33 ng/ml), with all proteins prepared as 2× dilution because they were later transferred to the plates containing the cells. Controls included DMEM, DMEM-1% FBS, and IL6Ralpha-IL6-His6 in 0% FBS. The plates were incubated with the dilutions of proteins for 1 h at 37° C., after which 100 microliters of protein mixes were transferred to the starved cells.

On day 5, cells in each well were washed twice with 200 microliters of PBS, and then 100 microliters of a solution to measure acid phosphatase. The solution was 0.1 M sodium acetate pH 5.5, 0.1% Triton X-100, 2.5 mg/ml paranitrophenylphosphate. The plates were incubated at 37° C. for 1 hour, after which the reaction was stopped with 100 microliters of 0.1 N NaOH, and the plate was read at 410 nm.

Figure 10A:
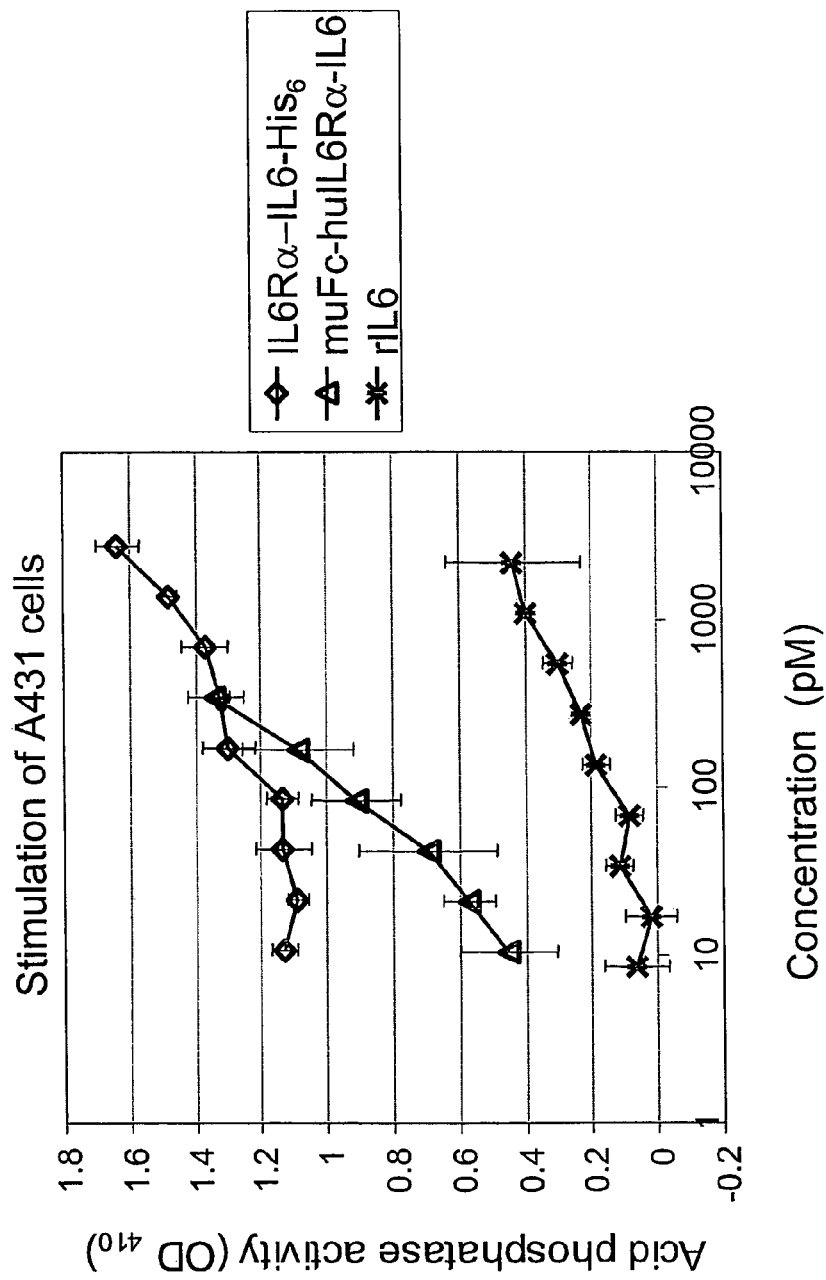
FIG. 10A depicts experimental results reflecting that the Fc-IL6Ralpha-IL6 fusion protein stimulates proliferation of A431 human epithelial carcinoma cells.
Figures 1, 10B:
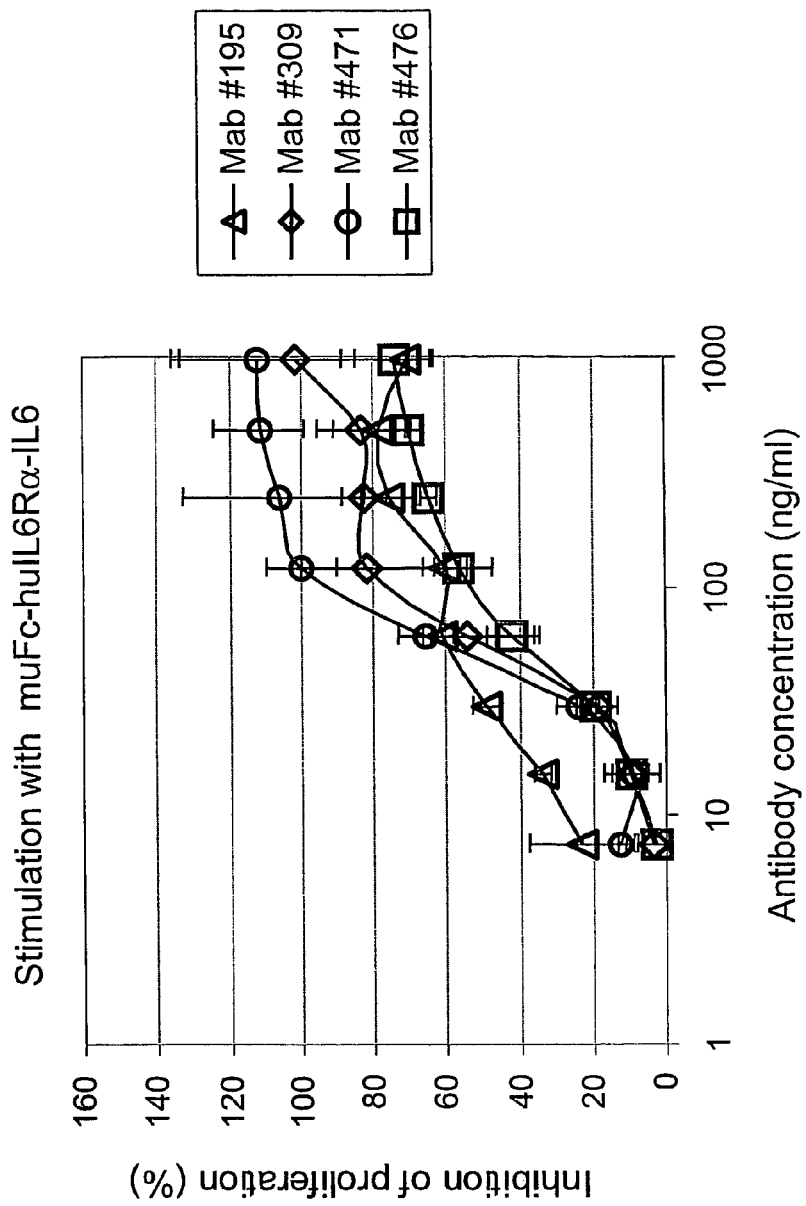
Figures 2, 10B:
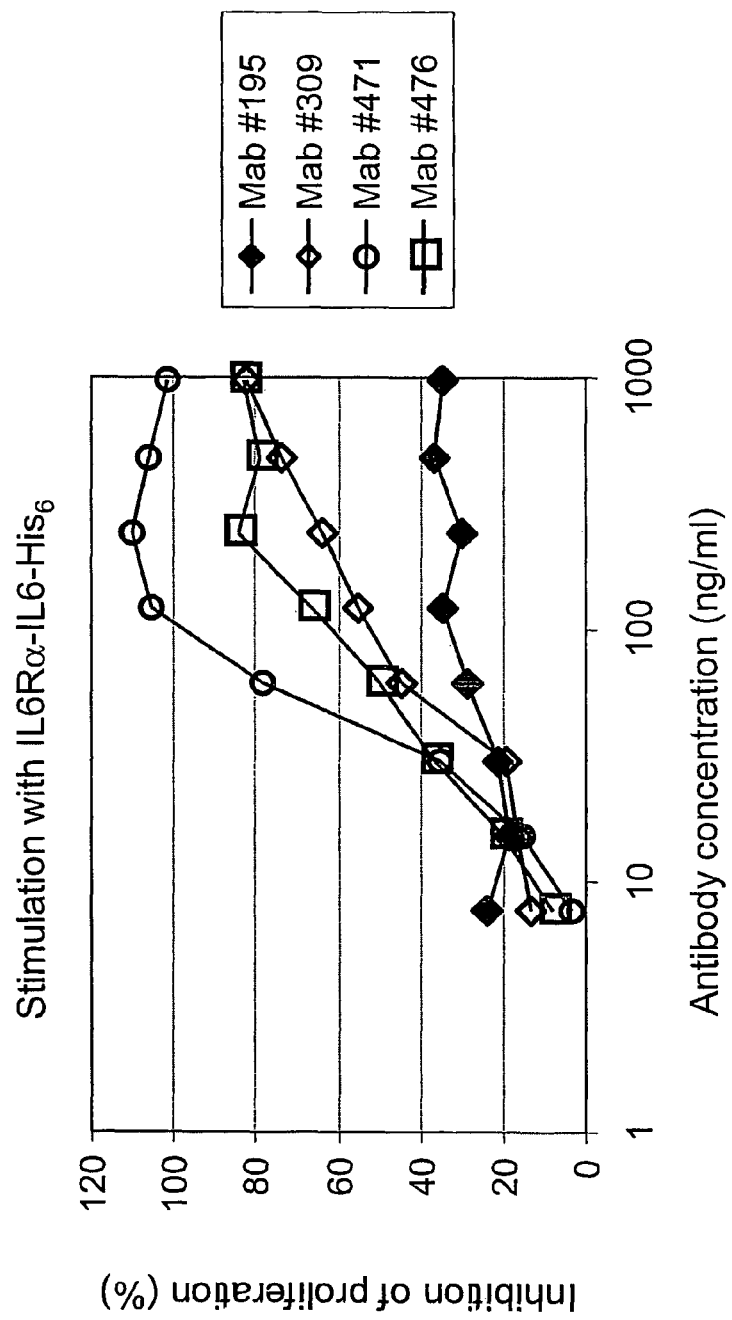

Typical results were illustrated in FIGS. 10A, 10B-1 and 10B-2. As shown in FIGS. 10B-1 and 10B-2, the antibodies of the invention inhibit the proliferation of A431 human epithelial carcinoma cells seen with stimulation by IL-6/IL-6Ralpha fusion protein. A typical result of proliferation of A431 cells stimulated by IL-6/IL-6Ralpha fusion protein is shown in FIG. 10A.

Example 4

V Region Sequences of Antibodies that Bind to IL-6 and Block Interaction with Gp130

The V region sequences of monoclonal antibodies Mab#195, Mab#309, Mab#471, and Mab#476 were determined according to standard procedures. mRNA of each hybridoma clones were purified using the Dynabeads Direct mRNA kit (Dynal) following the manufacturer's instructions. Reverse-Transcription PCR (RT-PCR) was performed to obtain cDNA using the BD SMART™ cDNA synthesis kit (BD Clontech) according to manufacturer manual. Two successive PCRs were performed using the cDNA as template, nested oligonucleotides and the polymerase KOD (EMD Biosciences) as instructed by the manufacturer. The 3' oligonucleotides were specific to amplify VH and Vk of a mouse IgG γ1 antibody while the 5' oligonucleotides were nested oligonucleotides from the BD SMART™ cDNA synthesis kit (sequences added to the 5' during the RT-PCR).

For example, heavy chain and light chain V regions were obtained by PCR amplification using a constant region primer and a V region primer with the oligonucleotides sequences and conditions indicated below.

VH Amplification:

```
PCR#1
5' Oligonucleotide #1:
                                        (SEQ ID NO:43)
5' ACAACGCAGAGTACGCGG 3'

3' Oligonucleotide #1:
                                        (SEQ ID NO:44)
5' AGGAGAGCTGGGAAGGTGTG 3'

PCR#2
5' Oligonucleotide #2:
                                        (SEQ ID NO:45)
5' ACAACGCAGAGTACGCGG 3'

3' Oligonucleotide #2:
                                        (SEQ ID NO:46)
5' TAGCCCTTGACCAGGCATCCC 3'
```

Vk Amplification:

```
PCR#1
5' Oligonucleotide #1:
                                        (SEQ ID NO:47)
5' ACAACGCAGAGTACGCGG 3'

3' Oligonucleotide #1:
                                        (SEQ ID NO:48)
5' CTGCCATCAATCTTCCACTTGAC 3'

PCR#2
5' Oligonucleotide #2:
                                        (SEQ ID NO:49)
5' CATCCTCTCTTCCAGCTCTC 3'

3' Oligonucleotide #2:
                                        (SEQ ID NO:50)
5' CTGAGGCACCTCCAGATG 3'
```

| | | |
|---|---|---|
| PCR #1 | 2 min | 94° C. |
| | 30 sec | 90° C. |
| | 30 sec 65° C. | x 30 |
| | 30 sec | 72° C. |
| | | 72° C. |
| PCR #2 | 2 min | 94° C. |
| | 30 sec | 90° C. |
| | 30 sec 65° C. | x 40 |
| | 30 sec | 72° C. |
| | | 72° C. |

PCR products were purified from agarose gel using the QIAquick gel extraction kit (QIAGEN) and subcloned into the TOPO blunt pCR4 vector (Invitrogen) for sequencing. Sequences were obtained using primers T7 and T3 and standard sequencing procedures.

The light chain and heavy chain sequences including the V region sequences of Mab#195, Mab#309, Mab#471, and Mab#476 are shown below.

MAb #195 VH mature region
                                        (SEQ ID NO:33)
EVKLEESGGGLVQPGGSMKLSCVASGFTFSNYWMNWVRQSPEKGLEWVAE

IRLKSNNYATHYAESVKGRFTISRDDSKSSVYLQMNNLRAEDTGIYYCTR

EDYYGYPDYWGQGTTLTVSS

MAb #195 VK mature region
                                        (SEQ ID NO:29)
DIVLTQSPASLAVSLGQRATISCRASESVDNFGISFMNWFQQKPGQPPKL

LIYVASNQGSGVPARFSGSGSGTDFSLNIHPMEEDDTAMYFCQQSKEVPW

TFGGGTKLEIK

MAb #309 VH mature region
                                        (SEQ ID NO:34)
EVKLEESGGGLVQPGGSMKLSCVASGFTFSNYWMNWVRQSPEKGLEWVAE

IRLKSNKGATHYAESVKGRFTISRDDSKSSVYLQMNNLRAEDTGIYYCAS

LLYDGYLHWGQGTLVTVSA

MAb #309 VK mature region
                                        (SEQ ID NO:30)
DIVLTQSPASLAVSLGQRATISCRASESVGNFGISFMNWFQQKPGQPPKL

LIYTASNQGSGVPARFSGSGSGTDFSLNIHPMEEDDSAMYFCQQSKEVPW

TFGGGTKLEIK

MAb #471 VH mature region
                                        (SEQ ID NO:35)
EVKFEESGGGLVQPGGSMKLSCVASGFSFSNYWMNWVRQSPEKGLEWVAE

IRLTSNKQAIYYAESVKGRFTISRDDSKSSVYLQMNNLRAEDTGIYYCAS

LFYDGYLHWGQGTLVTVSA

MAb #471 VK mature region
                                        (SEQ ID NO:31)
DIVLTQSPASLAVSLGQRATISCRASESVGNFGISFMNWFQQKPGQPPKL

LIYTASNQGSGVPARFSGSGSGTDFSLNIHPMEEDDSAMYFCQQSKEIPW

TFGGGTKLEIK

MAb #476 VH mature region
                                        (SEQ ID NO:36)
EVKLEESGGGLVQPGGSMKLSCAASGFTFSDAWMDWVRQSPEKGLEWVAE

IRSKANNHATYYAESVKGRFTISRDDSKSSVYLQMNSLRAEDTGIYYCTT

PTLYGAMDYWGQGTSVTVSA

MAb #476 VK mature region
                                        (SEQ ID NO:32)
DIVLTQSPASLAVSLGQRATISCRASESVHNFGISFMNWFQQKPGQPPKL

LIYTASNQGSGVPARFSGSGSGTDFSLNIHPVEEDDTAMYFCQQGKEVPW

TFGGGTKLEIK

DNA encoding mAb #195 VH mature region
                                        (SEQ ID NO:51)
GAAGTGAAGCTTGAGGAGTCTGGAGGAGGCTTGGTGCAACCTGGAGGATC

CATGAAACTCTCCTGTGTTGCCTCTGGATTCACTTTCAGTAACTACTGGA

-continued

TGAACTGGGTCCGCCAGTCTCCAGAGAAGGGGCTTGAGTGGGTTGCTGAA

ATTAGATTGAAATCTAATAATTATGCAACACATTATGCGGAGTCTGTGAA

AGGGAGGTTCACCATCTCAAGAGATGATTCCAAAAGTAGTGTCTACCTGC

AAATGAACAACTTAAGAGCTGAAGACACTGGCATTTATTACTGTACCAGG

GAGGACTACTACGGCTACCCTGACTACTGGGGCCAAGGCACCACTCTCAC

AGTCTCCTCA

DNA encoding mAb #195 VK mature region
(SEQ ID NO:52)
GACATTGTGCTGACCCAGTCTCCAGCTTCTTTGGCTGTGTCTCTAGGTCA

GAGGGCCACCATCTCCTGCAGAGCCAGCGAAAGTGTTGATAATTTTGGCA

TTAGTTTTATGAACTGGTTCCAACAGAAACCTGGACAGCCACCCAAACTC

CTCATCTATGTTGCATCCAACCAAGGATCCGGGGTCCCTGCCAGGTTTAG

TGGCAGTGGGTCTGGGACAGACTTCAGCCTCAACATCCATCCTATGGAGG

AGGATGATACTGCAATGTATTTCTGTCAGCAAAGTAAGGAGGTTCCGTGG

ACGTTCGGTGGAGGCACCAAGCTGGAAATCAAA

DNA encoding mAb #309 VH mature region
(SEQ ID NO:53)
GAAGTGAAACTTGAGGAGTCTGGAGGAGGCTTGGTTCAACCTGGAGGATC

CATGAAACTCTCCTGTGTTGCCTCTGGATTCACTTTCAGTAACTACTGGA

TGAACTGGGTCCGCCAGTCTCCAGAGAAGGGGCTTGAGTGGGTTGCTGAA

ATTAGACTGAAATCTAATAAGGGTGCAACACATTATGCGGAGTCTGTGAA

AGGGAGGTTCACCATCTCAAGGATGATTCCAAAAGTAGTGTCTACCTGC

AAATGAACAACTTAAGAGCTGAAGACACTGGCATTTATTACTGTGCCAGC

CTTTTGTATGATGGTTACTTACATTGGGGCCAAGGGACTCTGGTCACTGT

CTCTGCA

DNA encoding mAb #309 VK mature region
(SEQ ID NO:54)
GACATTGTGCTGACCCAATCTCCAGCTTCTTTGGCTGTGTCTCTAGGGCA

GAGGGCCACCATCTCCTGCAGAGCCAGCGAAAGTGTTGGTAATTTTGGCA

TTAGTTTTATGAATTGGTTCCAACAGAAACCAGGACAGCCACCCAAACTC

CTCATCTATACTGCATCCAACCAAGGATCCGGGGTCCCTGCCAGGTTTAG

TGGCAGTGGGTCTGGGACAGACTTCAGCCTCAACATCCATCCTATGGAGG

AGGATGATTCTGCAATGTATTTCTGTCAGCAAAGTAAGGAGGTTCCGTGG

ACGTTCGGTGGAGGCACCAAACTGGAAATCAAA

DNA encoding mAb #471 VH mature region
(SEQ ID NO:55)
GAAGTGAAGTTTGAGGAGTCTGGAGGAGGCTTGGTGCAACCGGGAGGATC

CATGAAACTCTCCTGTGTTGCCTCTGGATTCAGTTTCAGTAACTACTGGA

TGAACTGGGTCCGCCAGTCTCCAGAGAAGGGGCTTGAGTGGGTTGCTGAA

ATTAGATTGACATCTAATAAGCAGGCAATATATTATGCGGAGTCTGTGAA

AGGGAGATTCACCATCTCAAGAGATGATTCCAAAAGTAGTGTCTACCTGC

AAATGAACAACCTAAGAGCTGAAGACACTGGCATTTATTACTGTGCCAGC

CTTTTCTATGATGGTTACTTACATTGGGGCCAAGGGACTCTGGTCACTGT

CTCTGCA

DNA encoding mAb #471 VK mature region
(SEQ ID NO:56)
GACATTGTGCTGACCCAATCTCCAGCTTCTTTGGCTGTGTCTCTAGGGCA

GAGGGCCACCATCTCCTGCAGAGCCAGCGAAAGTGTTGGTAATTTTGGCA

TTAGTTTTATGAACTGGTTCCAACAGAAACCAGGACAGCCACCCAAACTC

CTCATCTATACTGCATCCAACCAAGGATCCGGGGTCCCTGCCAGGTTTAG

TGGCAGTGGGTCTGGGACAGACTTCAGCCTCAACATCCATCCTATGGAGG

AGGATGATTCTGCAATGTATTTCTGTCAGCAAAGTAAGGAGATTCCGTGG

ACGTTCGGTGGAGGCACCAAACTGGAAATCAAA

DNA encoding mAb #476 VH mature region
(SEQ ID NO:57)
GAAGTGAAGCTTGAGGAGTCTGGAGGAGGCTTGGTGCAACCTGGAGGATC

CATGAAACTCTCTTGTGCTGCCTCTGGATTCACTTTTAGTGACGCCTGGA

TGGACTGGGTCCGCCAGTCTCCAGAGAAGGGGCTTGAGTGGGTTGCTGAA

ATTAGAAGTAAAGCTAATAATCATGCAACATACTATGCTGAGTCTGTGAA

AGGGAGGTTCACCATCTCAAGAGATGATTCCAAAAGTAGTGTCTACCTGC

AAATGAACAGCCTAAGAGCTGAAGACACTGGCATTTATTACTGTACGACC

CCTACTCTCTATGGCGCTATGGACTACTGGGGTCAAGGAACCTCAGTCAC

CGTCTCTGCA

DNA encoding mAb #476 VK mature region
(SEQ ID NO:58)
GACATTGTGCTGACCCAATCTCCAGCTTCTTTGGCTGTGTCTCTTGGGCA

GAGGGCCACCATCTCCTGCAGAGCCAGCGAAAGTGTTCATAATTTTGGCA

TTAGCTTTATGAACTGGTTCCAACAGAAACCAGGACAGCCACCCAAACTC

CTCATCTATACTGCATCCAACCAAGGATCCGGGGTCCCTGCCAGGTTTAG

TGGCAGTGGGTCTGGGACAGACTTCAGCCTCAACATCCATCCTGTGGAAG

AGGATGATACTGCAATGTATTTCTGTCAACAAGGTAAGGAGGTTCCGTGG

ACGTTCGGTGGAGGCACCAAGCTGGAAATCAAAC

The sequences of the V regions were aligned as shown in FIG. 2. Position variations among the sequences are indicated with arrows. The CDR regions are boxed. Based on the alignment, it is apparent that each antibody represents an independent isolate, and that the antibodies are similar to each other. Antibodies 309 and 471 are closely related, with only one substitution in the light chain, an Ile/Val substitution at position 98; and only six substitutions in the heavy chain. These antibodies may derive from an original IgM clone that diversified through somatic mutation and thus might not be truly independent.

Antibodies 195 and 476 are more similar to each other than to antibodies 309 and 471. Antibodies 195 and 476 differ at 5 positions in the light chain and 18 positions in the heavy chain. Analysis of the CDR3 in the heavy chain of the antibodies 195 and 476 suggested that these chains were formed by independent V-D-J joining events and thus represent antibodies deriving from independent IgM parents. Thus, the antibody sequences in FIG. 2 represent at least 3 independent selections of antibodies that bind to human IL-6 and block the interaction with gp130.

Example 5

Pharmacokinetic Properties of Antibodies that Bind to IL-6 and Block Interaction with Gp130

Figure 11:
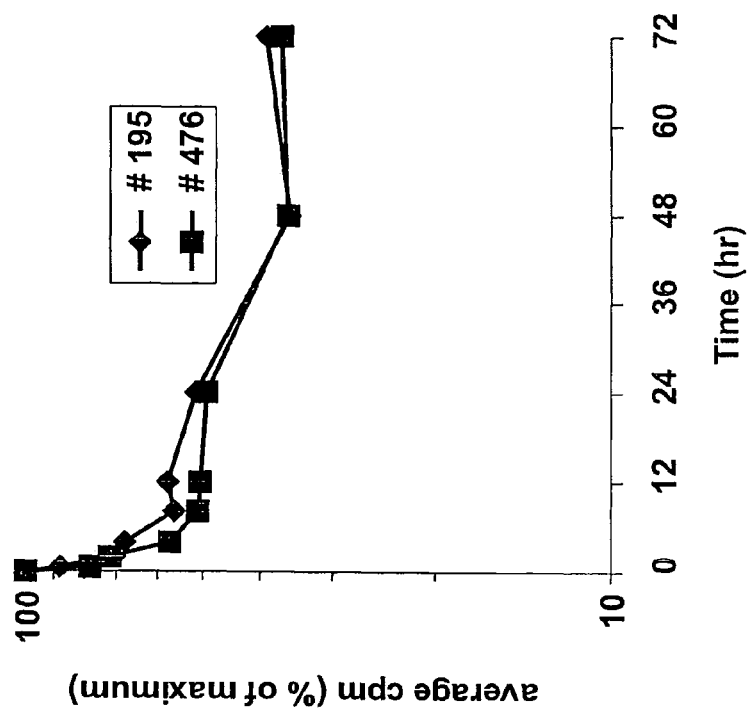
FIG. 11 illustrates pharmacokinetic properties of exemplary antibodies of the invention.

The serum half-life of antibodies 195 and 476 in mice was determined. Antibodies 195 and 476 were labeled with $^{125}$I according to standard procedures. About 25 micrograms of labeled antibody protein was injected intravenously into Balb/C mice, and blood samples were withdrawn at various times including 12, 24, 48, and 72 hours after injection. Levels of radioactivity in whole blood samples were determined. Based on this analysis, the elimination half-life was about 5 days for each antibody. Exemplary Data are shown in FIG. 11.

Example 6

In Vivo Inhibition of Haptoglobin Secretion

The antibodies of the invention were selected specifically for their ability to inhibit the binding of IL-6 to the receptor subunit gp130. In this experiment, using an assay measuring haptoglobin secretion induced by administration of a soluble IL-6Ralpha/IL-6 complex, the ability of antibody Mab#471 and a commercial anti IL-6 antibody to block activation of a gp130-dependent pathway in vivo were compared.

On day 0, nine-week old female Balb/C mice (n=3 per treatment group) were injected intraperitoneally with 100 µg of either antibody Mab#471 or an anti-IL-6 commercial antibody from R&D Systems (R&D Systems MAb #206) in a 200 µl volume. Mice in positive and negative control groups received 200 µl PBS. After 24 hours, mice in the experimental and positive control groups were administered 4 µg muFc-IL6Ralpha-IL6 intra-peritoneally in a 200 µl volume to induce haptoglobin secretion, and mice in the negative control group were administered 200 µl PBS. At 0, 8, and 24 hours after treatment, approximately 100 µl of blood was obtained from each mouse by retro-orbital bleeding, and the plasma fraction was isolated. Haptoglobin concentration in the plasma fraction was determined using a murine haptoglobin ELISA kit (Immunology Consultants Laboratory, Inc., Newberg, Oreg., Cat # E90HPT), following manufacturer's instructions.

Figure 12:
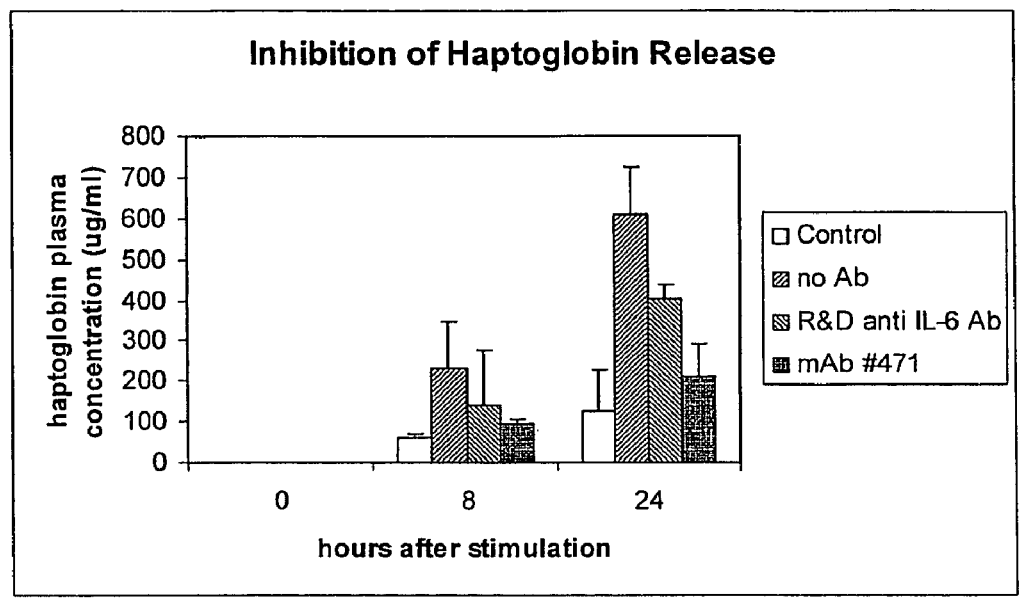
FIG. 12 shows an experimental result reflecting in vivo inhibition of haptoglobin secretion by exemplary antibodies of the invention, using procedures described in Example 6.

As shown in FIG. 12, haptoglobin levels in antibody Mab#471-treated mice were significantly less, about 30% of the level seen in the positive control group at 24 hours, and also significantly lower than in mice treated with the commercial antibody MAb #206. The increased levels of haptoglobin seen in mice of the negative control group were likely due to irritation caused by repeated retro-orbital bleeding procedure. Thus, the actual inhibition of haptoglobin secretion specifically caused by Fc-IL6Ralpha-IL6 is even greater than 70%, when the background of haptoglobin secretion seen in the control mice is subtracted. These results demonstrate that the antibody of the invention, e.g., antibody #471, which binds to IL-6 and blocks its interaction with the gp130 receptor subunit, is effective at inhibiting gp130-dependent signaling pathways that can be activated by a pre-formed IL-6Ralpha/IL-6 complex.

Example 7

Anti-Tumor Activity In Vivo

Figure 13:
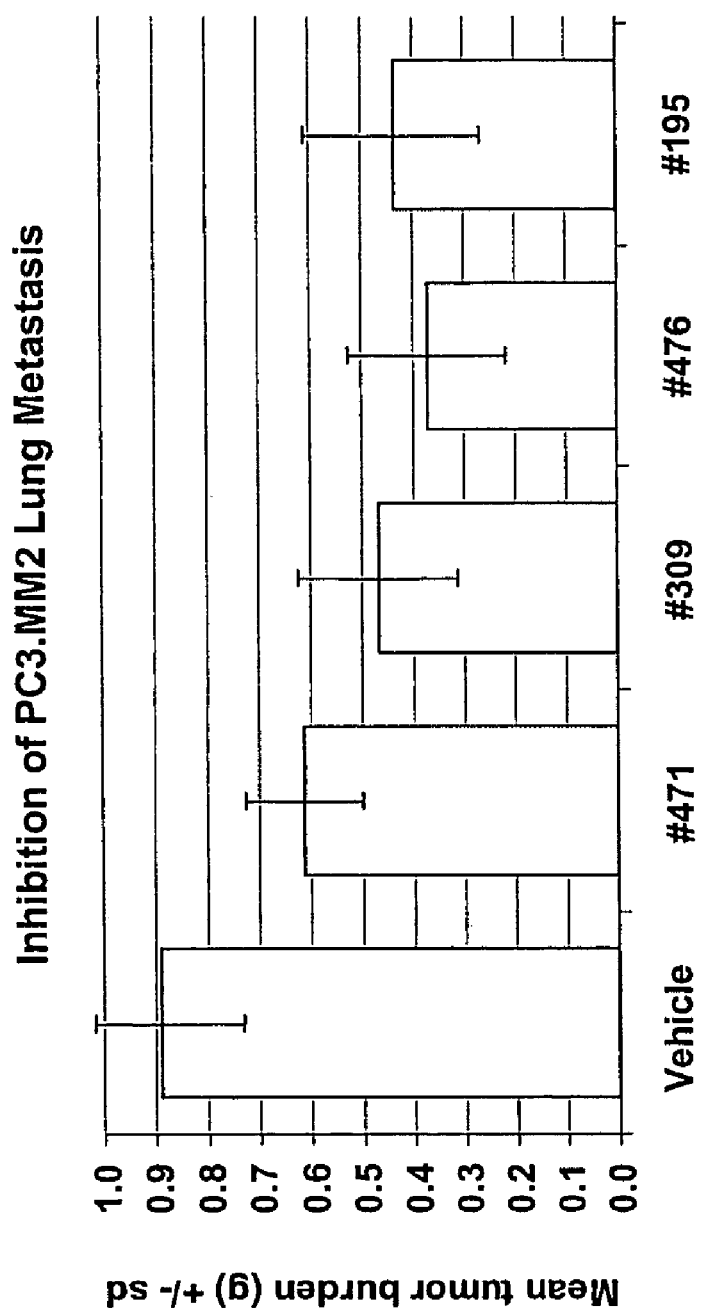
FIG. 13 shows an experimental result reflecting inhibition of lung metastasis by exemplary antibodies of the invention.

Antibodies Mab#195, Mab#309, Mab#471 and Mab#476 were tested for anti-tumor activity in vivo. A lung metastasis model was set up in SCID mice using PC3-MM2 cells which secrete IL-6 and for which IL-6 is a growth factor. About $2.0 \times 10^6$ PC3-MM2 cells were injected i.v. into each mouse. After 11 days the mice were treated with five daily doses of 5 µg/ml of the monoclonal antibodies Mab#195, Mab#309, Mab#471 and Mab#476. Typical results are shown in FIG. 13. As illustrated in FIG. 13, antibodies Mab#195, Mab#309, Mab#471 and Mab#476 inhibit lung metastases in mice.

Another experiment was done using antibody treatment after only 5 days post cell injection, instead of the usual 10 days. Similar results were obtained.

Example 8

Construction of Anti-IL-6 Antibodies with Human Constant Regions

A chimeric antibody against IL-6 that includes the V regions from antibody Mab#471 and human constant regions was constructed by techniques as described in U.S. Pat. No. 6,969,517, to Gillies et al., the teachings of which are hereby incorporated by reference. DNA sequences encoding the V regions of Mab#471 were obtained by PCR amplification using the following oligonuceotides. The lowercase regions are for adapters and the uppercase regions are V region specific.

```
VL forward (with Afl II site):
                                 (SEQ ID NO:59)
cttaagcGACATTGTGCTGACCCAATC VL reverse (with Bgl II site):
                                 (SEQ ID NO:60)
agatctacttacgTTTGATTTCCAGTTTGGTGCC VH forward (with Afl II site):
                                 (SEQ ID NO:61)
cttaagcGAAGTGAAGTTTGAGGAGTC VH reverse (with Hind III site):
                                 (SEQ ID NO:62)
aagcttacttaccTGCAGAGACAGTGACCAG
```

The resulting mouse-derived sequences were inserted into an antibody expression vector as described in U.S. Pat. No. 6,969,517, Example 3, to generate a expression plasmid encoding a chimeric antibody with a human kappa light chain and a human IgG1 heavy chain.

In order to obtain stably transfected human cell clones, the plasmid DNA was introduced into the mouse myeloma NS/0 cells by electroporation as described below. NS/0 cells were grown in Dulbecco's modified Eagle's medium supplemented with 10% fetal bovine serum. About $5 \times 10^6$ cells were washed once with PBS and re-suspended in 0.5 ml phosphate buffer solution (PBS). Ten µg of linearized plasmid DNA was then incubated with the cells in a Gene Pulser® Cuvette (0.4 cm electrode gap, BioRad) for 10 minutes on ice. Electroporation was performed using a Gene Pulser® (BioRad) with settings at 0.25 V and 500 µF Cells were allowed to recover for 10 minutes on ice, after which they were resuspended in growth medium and then plated onto two 96-well plates. Stably transfected clones were selected by growth in the presence of 100 nM methotrexate (MTX), which was introduced two days post-transfection. The cells were fed every 3 days for two to three more times, and MTX-resistant clones appeared in 2 to 3 weeks. Supernatants from clones were assayed by anti-human Fc ELISA to identify high producers (Gillies et al. (1989) *J. Immunol. Methods,* 125:191). High producing clones were isolated and propagated in growth medium containing 100 nM MTX.

To confirm that the chimeric 471 antibody retained the desired properties, this molecule was tested for inhibition of haptoglobin production in vitro, as described in Example 6 above; for inhibition of proliferation of LP-1 myeloma cells; and for inhibition of haptoglobin production in vivo, as described in Example 6 above. As controls, the anti-IL-6 antibodies Mab 206 (R&D Systems; Minneapolis, Minn.) and CNTO-328 (Zaki M. H. et al., *Int. J. Cancer*, (2004) 111:592-5) were used.

Effects of chimeric 471 antibody (Ch anti IL-6 #471) produced from a stably transfected cell line on haptoglobin secretion are indicated in the table below. Similar results were obtained from chimeric 471 antibody produced from transiently transfected cells.

|  | Haptoglobin Inhibition | | |
|---|---|---|---|
|  | IC50(ng/ml) AVG | SD | Repetitions |
| Ch anti IL-6 # 471 + IL-6 | 1.89 | 0.42 | 2 |
| MAb 206 + IL-6 | 16.08 | 12.48 | 2 |
| Ch anti IL-6 CNTO-328 + IL-6 | 5.19 | 0.88 | 2 |
| Ch anti IL-6 # 471 + IL-6Rα-IL-6 | 1.31 | 0.57 | 3 |
| MAb 206 + IL-6Rα-IL-6 | 4.80 | 2.64 | 3 |
| Ch anti IL-6 CNTO-328 + IL-6Rα-IL-6 | >333 | 0.00 | 3 |

The results indicate that the chimeric antibody 471 is effective at inhibiting the function of both IL-6 and the IL-6/IL-6Ralpha fusion protein. In contrast, Mab#206 is relatively ineffective at inhibiting-haptoglobin secretion stimulated by either IL-6 or IL-6/IL-6Ralpha fusion protein, and CNTO-328 shows a profound defect in inhibition of haptoglobin secretion stimulated by IL-6/IL-6Ralpha fusion protein.

The chimeric antibody 471 was also tested for its ability to inhibit proliferation of LP-1 myeloma cells. LP-1 is a human myeloma cell line whose proliferation can be stimulated by IL-6.

The LP-1 cell proliferation assay was performed as follows. LP-1 cells were purchased from the DSMZ (cat # ACC 41) (Georgii-Hemming P. et al. *Blood* (1996) 88:2250). Cells were cultured in 20% FBS and then starved for 3 days in 1% FBS media before the proliferation assay. After starvation, the cells were washed three times and diluted into 0.5% FBS containing media. Anti-IL-6 antibodies were diluted and incubated in the plate with either 0.005 ng/ml IL-6 or 0.05 ng/ml Fc-IL6Ralpha-IL6 fusion protein stimulation for one hour at 37° C. 5% $CO_2$. Then about 100,000 cells in 100 µl were added to wells of a 96 well plate with 100 µl of diluted proteins plus stimulation, incubated for 56 hours, and then $^3H$ Thymidine was added for the last 16 hours. The cells were then harvested from the wells with water onto glass microfiber filter plates and radioactivity was measured by liquid scintillation counting.

The table below shows typical results with chimeric 471 antibody produced from a stably transfected cell line. Similar results were obtained from chimeric 471 antibody produced from transiently transfected cells.

|  | LP-1 Proliferation | | |
|---|---|---|---|
|  | IC50(ng/ml) AVG | SD | Repetitions |
| Ch anti IL-6 # 471 + IL-6 | 5.15 | 2.27 | 3 |
| MAb 206 + IL-6 | 341.87 | 234.58 | 3 |
| Ch anti IL-6 CNTO-328 + IL-6 | 10.07 | 1.42 | 3 |
| Ch anti IL-6 # 471 + IL-6Rα-IL-6 | 0.39 | 0.36 | 3 |
| MAb 206 + IL-6Rα-IL-6 | 7.77 | 8.08 | 3 |
| Ch anti IL-6 CNTO-328 + IL-6Rα-IL-6 | 1608 | 539 | 3 |

The results indicate that the chimeric 471 antibody is effective at inhibiting LP-1 proliferation stimulated by both IL-6 and the IL-6/IL-6Ralpha fusion protein. In contrast, Mab#206 is ineffective at inhibiting LP-1 proliferation stimulated by IL-6, and CNTO-328 shows a profound defect in inhibition of LP-1 proliferation stimulated by IL-6/IL-6Ralpha fusion protein.

The inhibitory effects of chimeric 471 antibody and various control antibodies on haptoglobin secretion in vivo were also tested as described in Example 6. The following results were obtained.

|  | 0 hours ug/ml Hapatoglobin | | 8 Hours ug/ml Hapatoglobin | | 24 Hours ug/ml Hapatoglobin | | 8 Hours % Inhibition | 24 hours % Inhibition | TTEST VS PBS | |
|---|---|---|---|---|---|---|---|---|---|---|
|  | AVG | SD | AVG | SD | AVG | SD |  |  | 8 Hrs | 24 Hrs |
| No treatment | 0.8 | 0.1 | 0.8 | 0.9 | 4.2 | 4.7 |  |  |  |  |
| PBS | 0.6 | 0.1 | 24 | 17 | 113 | 170 |  |  |  |  |
| Fc-IL6Rα-IL6 | 0.8 | 0.1 | 463 | 128 | 994 | 125 |  |  |  |  |
| Ch 471 | 1.0 | 0.2 | 83 | 61 | 214 | 176 | 82 | 78 | 0.01 | 0.00 |
| CNTO 328 | 0.8 | 0.2 | 406 | 58 | 1027 | 91 | 12 | −3 | 0.52 | 0.73 |
| R&O MAB206 | 0.6 | 0.3 | 297 | 71 | 672 | 58 | 36 | 32 | 0.12 | 0.02 |
| Anti-CD19 chB4 | 0.8 | 0.1 | 487 | 138 | 1335 | 346 | −5 | −34 | 0.86 | 0.18 |

These results indicate that chimeric 471 antibody (referred to as Ch 471 in the above table) strongly blocks haptoglobin secretion stimulated by an IL-6/IL-Ralpha complex, while control antibodies such as Mab#206 and CNTO-328 are less effective or ineffective at inhibition of haptoglobin secretion.

Example 9

Treatment of a Human Patient with Antibodies and Methods of the Invention

The anti-IL-6 antibodies of the invention are used to treat human diseases and disorders as follows. In general, the preferred method of administration is by i.v. infusion or i.v. injection, although subcutaneous injection, inhalation, oral delivery, and other methods are also possible. Administration about once every 2, 3 or 4 weeks is used, although the frequency of administration may vary depending on the needs of the patient. A typical dose is about 100 to 800 mgs for an adult human. Treated patients are monitored for signs of infection that may result from immunosuppression.

For example, a patient with Castleman's disease is treated with chimeric 471 antibody of the invention about once every two weeks at a dose of about 8 mg/kg, with administration by drip infusion.

A patient with rheumatoid arthritis is treated with chimeric 471 antibody about once every four weeks at a dose of about 8 mg/kg, with administration by drip infusion. Progression of joing destruction is found to be significantly inhibited by monotherapy, even when compared to disease-modifying anti-rheumatic drugs.

A patient with Crohn's disease is treated with chimeric 471 antibody about once every four weeks at a dose of about 8 mg/kg, with administration by drip infusion.

A patient with multiple myeloma is treated with chimeric 471 antibody about once every three weeks at a dose of about 8 mg/kg, with administration by drip infusion. Treatment with chimeric 471 is combined with a standard-of-care treatment for multiple myeloma as determined by a physician as appropriate for the patient.

A patient with advanced metastatic prostate cancer, with a history of treatment by conventional chemotherapy, is treated with chimeric 471 antibody about once every three weeks at a dose of about 8 mg/kg, with administration by drip infusion. Treatment with chimeric 471 antibody is combined with a standard-of-care treatment for prostate cancer as determined by a physician as appropriate for the patient. Non-steroidal anti-inflammatory drugs, for example Naproxen™ are also prescribed. As a result of prior chemotherapy, the patient has depressed white cells and low levels of naïve T cells. The patient is monitored particularly closely for infection resulting from immunosuppression and is given prophylactic antibiotics. It is found that the treatment has a positive effect on cachexia-type symptoms, such as bone loss.

A patient with hormone-refractory breast cancer is treated with chimeric 471 antibody about once every three weeks at a dose of about 8 mg/kg by drip infusion. Treatment with chimeric 471 antibody is combined with a standard-of-care treatment for advanced breast cancer as determined by a physician as appropriate for the patient. Non-steroidal anti-inflammatory drugs, for example Naproxen™ are also prescribed.

In an alternative treatment strategy, a patient with advanced hormone-refractory prostate cancer or advanced hormone-refractory breast cancer is treated with chimeric 471 antibody about once every three weeks at a dose of about 8 mg/kg, in combination with an immunocytokine such as KS-IL2. These two agents may be co-administered by drip infusion. Prior to the treatment, the patient is dosed with an immunostimulatory amount of cyclophosphamide. Non-steroidal anti-inflammatory drugs, for example Naproxen™ are also prescribed. Without wishing to be bound by theory, the combination of an anti-IL6 antibody of the invention and an immunocytokine such as KS-IL2 is particularly effective, in part because IL-6 causes a suppression of IL-12 signaling and TH1 responses, and the antibodies of the invention reverse this inhibition.

A patient with a B cell lymphoma is treated is treated with chimeric 471 antibody about once every three weeks at a dose of about 8 mg/kg, optionally in combination with an antibody such as Rituxan™ at about 375 milligrams per square meter of body surface area, which is administered every week. Alternatively, in the case of a patient with refractory lymphoma, treatment with chimeric 471 antibody is combined with a radioimmunoconjugate such as Bexxar™ or Zevalin™.

INCORPORATION BY REFERENCE

All sequence accession numbers, publications and patent documents cited in this application are incorporated by reference in their entirety for all purposes to the same extent as if the contents of each individual publication or patent document are incorporated herein.

I claim:

1. A method for treating an IL-6-expressing cancer in a patient, the method comprising administering to the patient a protein comprising an antibody variable region,
    wherein the antibody variable region binds to an epitope on IL-6 such that the binding sterically blocks an interaction between IL-6 and gp130, and
    wherein the antibody variable region does not sterically block an interaction between IL-6 and IL-6Ralpha.

2. The method of claim 1, wherein the protein is an antibody or a fragment thereof.

* * * * *